(12) United States Patent
Yerkes et al.

(10) Patent No.: US 8,912,121 B2
(45) Date of Patent: Dec. 16, 2014

(54) HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND CERTAIN PS II INHIBITORS

(71) Applicant: Dow Agrosciences LLC, Indianapolis, IN (US)

(72) Inventors: Carla N. Yerkes, Crawfordsville, IN (US); Richard K. Mann, Franklin, IN (US); Norbert M. Satchivi, Westfield, IN (US); Paul R. Schmitzer, Indianapolis, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/840,488

(22) Filed: Mar. 15, 2013

(65) Prior Publication Data
US 2014/0031222 A1     Jan. 30, 2014

Related U.S. Application Data

(60) Provisional application No. 61/675,089, filed on Jul. 24, 2012.

(51) Int. Cl.
| | |
|---|---|
| A01N 25/26 | (2006.01) |
| A01N 43/40 | (2006.01) |
| A01N 43/46 | (2006.01) |
| A01N 43/78 | (2006.01) |
| A01N 43/88 | (2006.01) |
| A01N 37/34 | (2006.01) |
| A01N 43/70 | (2006.01) |
| A01N 47/32 | (2006.01) |
| A01N 43/82 | (2006.01) |
| A01N 47/30 | (2006.01) |
| A01N 43/66 | (2006.01) |
| A01N 43/58 | (2006.01) |
| A01N 37/22 | (2006.01) |

(52) U.S. Cl.
CPC .............. *A01N 43/40* (2013.01); *A04N 43/707* (2013.01); *A01N 43/78* (2013.01); *A01N 43/88* (2013.01); *A01N 37/34* (2013.01); *A01N 43/70* (2013.01); *A01N 47/32* (2013.01); *A01N 43/82* (2013.01); *A01N 47/30* (2013.01); *A01N 43/66* (2013.01); *A01N 43/58* (2013.01); *A01N 37/22* (2013.01)
USPC ........................... 504/100; 504/134; 504/136

(58) Field of Classification Search
CPC ........ A01N 25/26; A01N 43/40; A01N 43/46
See application file for complete search history.

(56) References Cited

U.S. PATENT DOCUMENTS

| | | | |
|---|---|---|---|
| 7,314,849 B2 * | 1/2008 | Balko et al. ................... | 504/244 |
| 7,622,641 B2 | 11/2009 | McCutchen et al. | |
| 2009/0062121 A1 | 3/2009 | Satchivi et al. | |
| 2010/0137137 A1 | 6/2010 | Rosinger et al. | |
| 2011/0082162 A1 | 4/2011 | Lorsbach et al. | |
| 2011/0207607 A1 | 8/2011 | Satchivi et al. | |
| 2012/0115727 A1 | 5/2012 | Satchivi et al. | |
| 2012/0190551 A1* | 7/2012 | Yerkes et al. ................. | 504/242 |
| 2013/0109569 A1* | 5/2013 | Dave et al. .................... | 504/130 |
| 2013/0310256 A1 | 11/2013 | Yerkes et al. | |
| 2014/0031210 A1 | 1/2014 | Yerkes et al. | |
| 2014/0031211 A1 | 1/2014 | Yerkes et al. | |
| 2014/0031212 A1 | 1/2014 | Yerkes et al. | |
| 2014/0031213 A1 | 1/2014 | Yerkes et al. | |
| 2014/0031214 A1 | 1/2014 | Yerkes et al. | |
| 2014/0031215 A1 | 1/2014 | Yerkes et al. | |
| 2014/0031216 A1 | 1/2014 | Yerkes et al. | |

(Continued)

FOREIGN PATENT DOCUMENTS

WO    WO 2007/082098      7/2007

OTHER PUBLICATIONS

Thomas, S., Written Opinion of the International Search Authority for PCT/US2013/051297, Dec. 3, 2013, pp. 1-5, ISA/US.

(Continued)

*Primary Examiner* — Alton Pryor
(74) *Attorney, Agent, or Firm* — Michael R. Asam

(57) ABSTRACT

Provided herein are synergistic herbicidal compositions containing (a) a compound of formula (I):

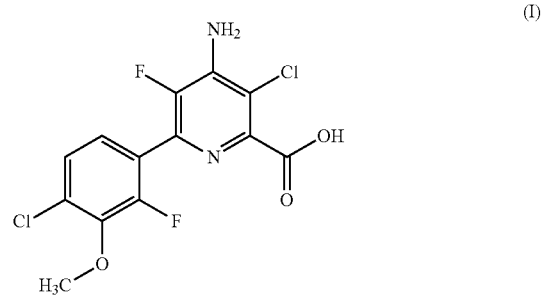

(I)

or an agriculturally acceptable salt or ester thereof and (b) a PS II inhibitor, including but not limited to, atrazine, bentazon-sodium, bromoxynil, chlorotoluron, cyanazine, diuron, hexazinone, ioxynil, isoproturon, linuron, methibenzuron, metribuzin, propanil, pyridate, siduron, simazine, simetryne, tebuthiuron and terbuthylazine, or a salt or ester thereof. The compositions and methods provided herein provide control of undesirable vegetation, e.g., in direct-seeded, water-seeded and transplanted rice, cereals, wheat, barley, oats, rye, sorghum, corn or maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) or rights of way (ROW).

16 Claims, No Drawings

(56) References Cited

U.S. PATENT DOCUMENTS

| | | |
|---|---|---|
| 2014/0031217 A1 | 1/2014 | Yerkes et al. |
| 2014/0031218 A1 | 1/2014 | Mann et al. |
| 2014/0031219 A1 | 1/2014 | Yerkes et al. |
| 2014/0031220 A1 | 1/2014 | Yerkes et al. |
| 2014/0031221 A1 | 1/2014 | Yerkes et al. |
| 2014/0031227 A1 | 1/2014 | Yerkes et al. |
| 2014/0031228 A1 | 1/2014 | Mann et al. |
| 2014/0031229 A1 | 1/2014 | Mann et al. |

OTHER PUBLICATIONS

Thomas, S., International Search Report for PCT/US2013/051297, Dec. 3, 2013, pp. 1-4, ISA/US.
Synthesis of Esters: Esterification Reactions, obtained via google.com U.S. Appl. No. 13/840,306, obtained online Mar. 8, 2014.
Chui, M.P., Non-Final Office Action in U.S. Appl. No. 13/840,306, Mar. 13, 2014, pp. 1-12, USPTO.
Pryor, A.N., Notice of Allowance and Fee(s) Due for U.S. Appl. No. 13/832,978, Apr. 9, 2014, pp. 1-13, USPTO.
Pryor, A.N., Notice of Allowance and Fee(s) Due for U.S. Appl. No. 13/833,315, May 12, 2014, pp. 1-8, USPTO.
Pryor, A.N., Notice of Allowance and Fee(s) Due for U.S. Appl. No. 13/833,315, Mar. 20, 2014, pp. 1-11, USPTO.
Pryor, A.N., Notice of Allowance and Fee(s) Due for U.S. Appl. No. 13/833,362, May 29, 2014, pp. 1-8, USPTO.
Pryor, A.N., Notice of Allowance and Fee(s) Due for U.S. Appl. No. 13/833,372, May 14, 2014, pp. 1-8, USPTO.
Pryor, A.N., Notice of Allowance and Fee(s) Due for U.S. Appl. No. 13/833,659, Mar. 17, 2014, pp. 1-12, USPTO.
Pryor, A.N., Notice of Allowance and Fee(s) Due for U.S. Appl. No. 13/833,923, May 2, 2014, pp. 1-9, USPTO.
Pryor, A.N., Notice of Allowance and Fee(s) Due for U.S. Appl. No. 13/833,965, Apr. 1, 2014, pp. 1-8, USPTO.
Pryor, A.N., Notice of Allowance and Fee(s) Due for U.S. Appl. No. 13/834,326, May 13, 2014, pp. 1-4, USPTO.
Pryor, A.N., Notice of Allowance and Fee(s) Due for U.S. Appl. No. 13/834,326, Apr. 2, 2014, pp. 1-9, USPTO.
Pryor, A.N., Notice of Allowance and Fee(s) Due for U.S. Appl. No. 13/836,653, Apr. 2, 2014, pp. 1-8, USPTO.
Pryor, A.N., Notice of Allowance and Fee(s) Due for U.S. Appl. No. 13/836,653, Jun. 17, 2014, pp. 1-5, USPTO.
Pryor, A.N., Notice of Allowance and Fee(s) Due for U.S. Appl. No. 13/837,990, Apr. 1, 2014, pp. 1-8, USPTO.
Pryor, A.N., Notice of Allowance and Fee(s) Due for U.S. Appl. No. 13/839,043, May 27, 2014, pp. 1-5, USPTO.
Pryor, A.N., Notice of Allowance and Fee(s) Due for U.S. Appl. No. 13/839,043, Mar. 24, 2014, pp. 1-8, USPTO.
Pryor, A.N., Notice of Allowance and Fee(s) Due for U.S. Appl. No. 13/840,303, Apr. 25, 2014, pp. 1-8, USPTO.
Pryor, A.N., Notice of Allowance and Fee(s) Due for U.S. Appl. No. 13/834,706, Mar. 12, 2014, pp. 1-13, USPTO.
Pryor, A.N., Notice of Allowance and Fee(s) Due for U.S. Appl. No. 13/840,346, Jun. 4, 2014, pp. 1-8, USPTO.
Pryor, A.N., Notice of Allowance and Fee(s) Due for U.S. Appl. No. 13/840,419, May 5, 2014, pp. 1-8, USPTO.
Pryor, A.N., Notice of Allowance and Fee(s) Due for U.S. Appl. No. 13/840,236, Apr. 25, 2014, pp. 1-8, USPTO.

* cited by examiner

HERBICIDAL COMPOSITIONS COMPRISING 4-AMINO-3-CHLORO-5-FLUORO-6-(4-CHLORO-2-FLUORO-3-METHOXYPHENYL)PYRIDINE-2-CARBOXYLIC ACID OR A DERIVATIVE THEREOF AND CERTAIN PS II INHIBITORS

PRIORITY CLAIM

This application claims the benefit of U.S. provisional patent application No. 61/675,089 filed on Jul. 24, 2012, this provisional application is incorporated herein by reference in its entirety.

FIELD

Provided herein are herbicidal compositions comprising and methods for controlling undesirable vegetation utilizing (a) 4-amino-3-chloro-5-fluoro-6-(4-chloro-2-fluoro-3-methoxyphenyl)pyridine-2-carboxylic acid or an agriculturally acceptable ester or salt thereof and (b) a photosystem (PS) II inhibitor selected from the group consisting of: atrazine, bentazon-sodium, bromoxynil, chlorotoluron, cyanazine, diuron, hexazinone, ioxynil, isoproturon, linuron, methibenzuron, metribuzin, propanil, pyridate, siduron, simazine, simetryne, tebuthiuron and terbuthylazine, or derivative, e.g., salt or ester thereof.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

Several embodiments are recited below. In the embodiments, the ratio of compound (a) to compound (b) can be expressed in units of weight to weight (g to g), gae/ha to gae/ha or gae/ha to gai/ha.

A first embodiment of the invention provided herein includes herbicidal compositions comprising an herbicidally effective amount of (a) a compound of the formula (I)

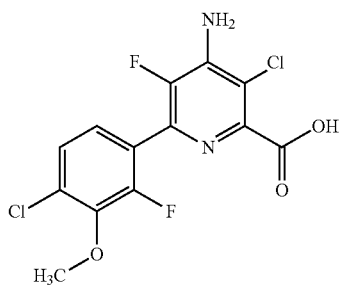

(I)

or an agriculturally acceptable salt or ester thereof and (b) atrazine, bentazon, bentazon-sodium, bromoxynil, chlorotoluron, cyanazine, diuron, hexazinone, ioxynil, isoproturon, linuron, methibenzuron, metribuzin, propanil, pyridate, siduron, simazine, simetryne, tebuthiuron or terbuthylazine or agriculturally acceptable salt or ester thereof.

A second embodiment includes a method of controlling undesirable vegetation which comprises contacting the vegetation or the locus thereof with or applying to the soil or water to prevent the emergence or growth of vegetation the composition of embodiment 1.

A third embodiment includes a method of controlling undesirable vegetation. The method comprises contacting the vegetation or the locus thereof with or applying to the soil or water to prevent the emergence or growth of vegetation, a herbicidally effective amount of (a) a compound of the formula (I)

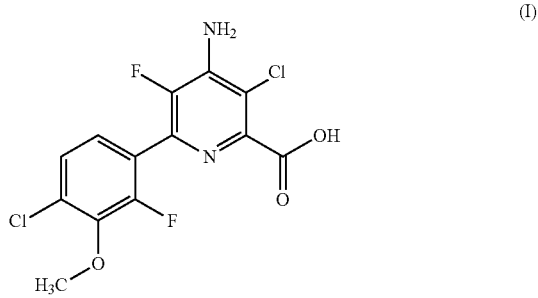 [SMILES: COc1c(Cl)ccc(-c2nc(C(=O)O)c(Cl)c(N)c2F)c1F]

(I)

or an agriculturally acceptable salt or ester thereof and (b) atrazine, bentazon, bentazon-sodium, bromoxynil, chlorotoluron, cyanazine, diuron, hexazinone, ioxynil, isoproturon, linuron, methibenzuron, metribuzin, propanil, pyridate, siduron, simazine, simetryne, tebuthiuron or terbuthylazine or agriculturally acceptable salt or ester thereof.

Provided herein are herbicidal compositions comprising and methods of controlling undesirable vegetation utilizing a herbicidally effective amount of (a) a compound of the formula (I)

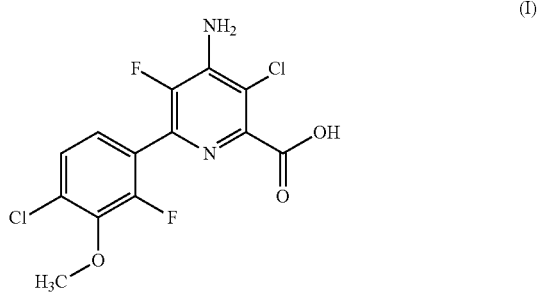 [SMILES: COc1c(Cl)ccc(-c2nc(C(=O)O)c(Cl)c(N)c2F)c1F]

(I)

or an agriculturally acceptable salt or ester of thereof, and (b) a PS II inhibitor selected from the group consisting of: atrazine, bentazon, bentazon-sodium, bromoxynil, chlorotoluron, cyanazine, diuron, hexazinone, ioxynil, isoproturon, linuron, methibenzuron, metribuzin, propanil, pyridate, siduron, simazine, simetryne, tebuthiuron and terbuthylazine, or derivative, e.g., salt or ester thereof. The compositions may also contain an agriculturally acceptable adjuvant or carrier.

DETAILED DESCRIPTION

Definitions

As used herein, the compound of formula (I) has the following structure:

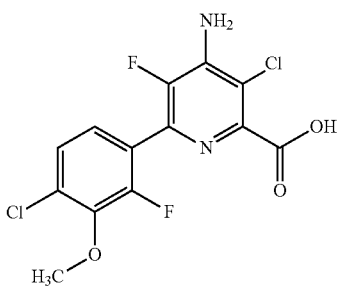

(I)

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

Atrazine is 6-chloro-N-ethyl-N'-(1-methylethyl)-1,3,5-triazine-2,4-diamine. Its herbicidal activity is described in *The Pesticide Manual*, Fifteenth Edition, 2009. Exemplary uses of atrazine include its use for pre-emergence and post-emergence control of broadleaf and grass weeds, e.g., in corn, sorghum, turf, sugar cane and other crops. Atrazine possesses the following structure:

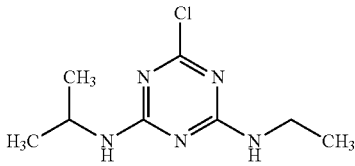

Bentazon is 3-(1-methylethyl)-1H-2,1,3-benzothiadiazin-4(3H)-one 2,2-dioxide. Its herbicidal activity is described in *The Pesticide Manual*, Fifteenth Edition, 2009. It is also known as bentazone. Bentazon has been used as its sodium salt, bentazon sodium. Exemplary uses of bentazon include its use for control of broadleaf and sedge weeds in broadleaf and grass crops. Bentazon possesses the following structure:

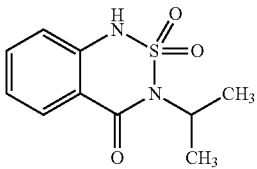

Bromoxynil is 3,5-dibromo-4-hydroxybenzonitrile. Its herbicidal activity is described in *The Pesticide Manual*, Fifteenth Edition, 2009. Exemplary uses of bromoxynil include its use for post-emergence control of broad-leaved weeds, e.g., in cereals, ryegrass-seed crops, turf, maize, and sorghum. It possesses the following structure:

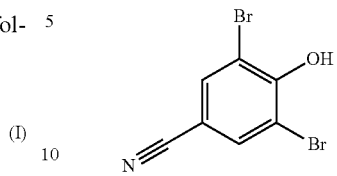

Chlorotoluron is N'-(3-chloro-4-methylphenyl)-N,N-dimethylurea. Its herbicidal activity is described in *The Pesticide Manual*, Fifteenth Edition, 2009. Exemplary uses of chlorotoluron include its use for control of broad-leaved and grass weeds, e.g., in winter cereals. It possesses the following structure:

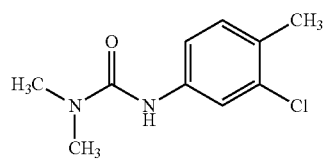

Cyanazine is 2-[[4-chloro-6-(ethylamino)-1,3,5-triazin-2-yl]amino]-2-methylpropanenitrile. Its herbicidal activity is described in *The Pesticide Manual*, Fifteenth Edition, 2009. Exemplary uses of cyanazine include its use for pre-emergent control of weeds in beans, maize and peas and post-emergent control of weeds in early barley and wheat. It possesses the following structure:

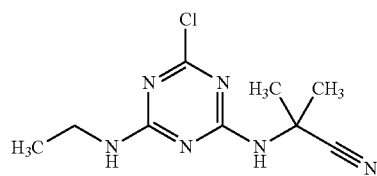 [SMILES: CCNc1nc(Cl)nc(NC(C)(C)C#N)n1]

Diuron is N'-(3,4-dichlorophenyl)-N,N-dimethylurea. Its herbicidal activity is described in *The Pesticide Manual*, Fifteenth Edition, 2009. Exemplary uses of diuron include its use for pre-emergence and post-emergence control of broadleaf and grass weeds in, e.g., corn, sorghum, sugar cane, citrus and other crops. Diuron possesses the following structure:

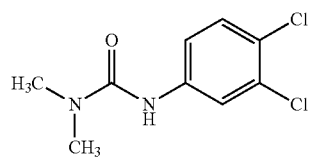

Hexazinone is 3-cyclohexyl-6-(dimethylamino)-1-methyl-1,3,5-triazine-2,4(1H,3H)-dione. Its herbicidal activity is described in *The Pesticide Manual*, Fifteenth Edition, 2009. Exemplary uses of hexazinone include its use for post-emergent control of annual, biennial and perennial weeds in alfalfa, pineapples, sugar cane and conifers. It possesses the following structure:

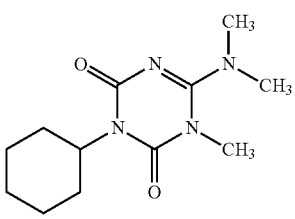 [SMILES: CN(C)c1nc(=O)n(C2CCCCC2)c(=O)n1C]

Ioxynil is 4-hydroxy-3,5-diiodobenzonitrile. Its herbicidal activity is described in *The Pesticide Manual*, Fifteenth Edition, 2009. Exemplary uses of ioxynil include its use for post-emergence control of annual broad-leaved weeds in cereals, onions, leeks, garlic, shallots, flax, sugar cane, forage grasses, lawns and newly-sown turf. It possesses the following structure:

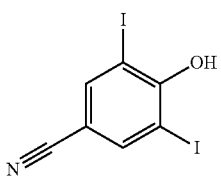

Isoproturon is N,N-dimethyl-N'-[4-(1-methylethyl)phenyl]urea. Its herbicidal activity is described in *The Pesticide Manual*, Fifteenth Edition, 2009. Exemplary uses of isoproturon include its use for pre-and post-emergence control of annual grasses and annual broad-leaved weeds, e.g., in spring and winter wheat, spring and winter barley, winter rye and tritcale. It possesses the following structure:

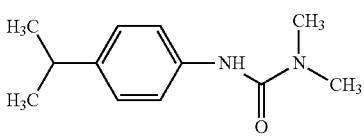

Linuron is N'-(3,4-dichlorophenyl)-N-methoxy-N-methylurea. Its herbicidal activity is described in *The Pesticide Manual*, Fifteenth Edition, 2009. Exemplary uses of linuron include its use for pre- and post-emergence control of annual grass and broad-leaved weeds, as well as seedling perennial weeds in asparagus, artichokes, carrots, parsley, fennel, parsnips, herbs and spices, celery, celeriac, onions, leeks, garlic, potatoes, peas, field beans, soya beans, cereals, maize, sorghum, cotton, flax, sunflowers, sugar cane, ornamentals, established vines, bananas, cassaya, coffee, tea, rice, peanuts, ornamental trees and shrubs, and other crops. It possesses the following structure:

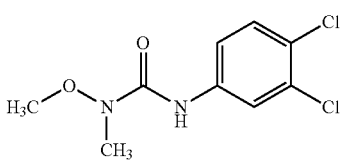

Methibenzuron is N-2-benzothiazolyl-N,N'-dimethylurea. Methibenzuron is also known as methabenzthiazuron. The herbicidal activity methibenzuron is described in *The Pesticide Manual*, Fifteenth Edition, 2009. Exemplary uses of methibenzuron include its use for broad-spectrum control of broad-leaved weeds and grasses, e.g., in cereals, legumes, maize, garlic and onions. It possesses the following structure:

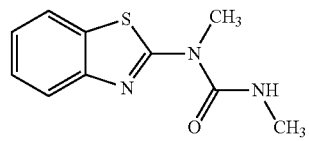

Metribuzin is 4-amino-6-(1,1-dimethylethyl)-3-(methylthio)-1,2,4-triazin-5(4H)-one. Its herbicidal activity is described in *The Pesticide Manual*, Fifteenth Edition, 2009. Exemplary uses of metribuzin include its use for pre-emergence and post-emergence control of broadleaf weeds, e.g., in soybeans, potatoes, corn, vegetables and other crops. Metribuzin possesses the following structure:

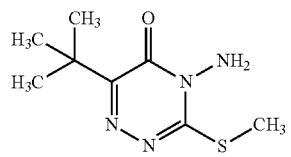

Propanil is N-(3,4-dichlorophenyl)propanamide. Its herbicidal activity is described in *The Pesticide Manual*, Fifteenth Edition, 2009. Exemplary uses of propanil include its use for post-emergence control of broadleaf and grass weeds in, e.g., rice. It possesses the following structure:

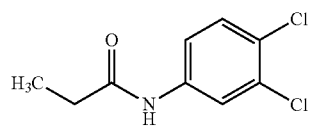

Pyridate is O-(6-chloro-3-phenyl-4-pyridazinyl) S-octyl carbonothioate. Its herbicidal activity is described in *The Pesticide Manual*, Fifteenth Edition, 2009. Exemplary uses of pyridate include its use for post-emergence control of annual broad-leaved weeds and grass weeds, e.g., in maize, sweet corn, oilseed rape, cereals, rice, peanuts and vegetables. It possesses the following structure:

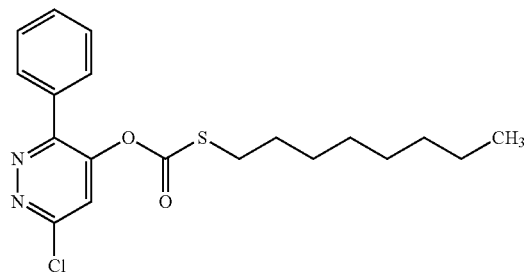 [SMILES: CCCCCCCCSC(=O)Oc1cc(Cl)nnc1-c1ccccc1]

Siduron is N-(2-methylcyclohexyl)-N'-phenylurea. Its herbicidal activity is described in *The Pesticide Manual*, Fifteenth Edition, 2009. Exemplary uses of siduron include its use for pre-emergence control of *Digitaria* spp. and annual grass weeds in, e.g., turf farms, grass seed production and established turf. It possesses the following structure:

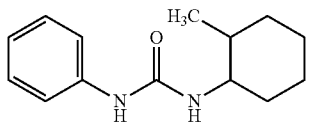 [SMILES: CC1CCCCC1NC(=O)Nc1ccccc1]

Simazine is 6-chloro-N,N'-diethyl-1,3,5-triazine-2,4-diamine. Its herbicidal activity is described in *The Pesticide Manual*, Fifteenth Edition, 2009. Exemplary uses of simazine include its use for control of germinating annual grasses and broad-leaved weeds in, e.g., pome fruit, stone fruit, bush and cane fruit, citrus fruit, vines, strawberries, nuts, olives, pineapples, field beans, French beans, pea, maize, sweet corn, asparagus, hops, alfalfa, lupins, oilseed rape, artichokes, sugar cane, cocoa, coffee, rubber, oil palms, tea, turf and ornamentals. It possesses the following structure:

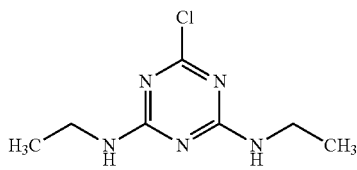

Simetryne is N,N'-diethyl-6-(methylthio)-1,3,5-triazine-2,4-diamine. Simetryne is simetryn. Its herbicidal activity is described in *The Pesticide Manual*, Fifteenth Edition, 2009. Exemplary uses of simetryn include its use for control of broad-leaved weeds, e.g., in rice. It possesses the following structure:

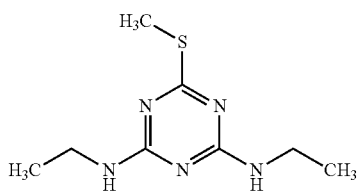

Tebuthiuron is N-[5-(1,1-dimethylethyl)-1,3,4-thiadiazol-2-yl]-N,N'-dimethylurea. Its herbicidal activity is described in *The Pesticide Manual*, Fifteenth Edition, 2009. Exemplary uses of tebuthiuron include its use for control of herbaceous and woody plants, annual weeds, and many perennial grass and undersirable woody plants in pastures and rangeland, and control of grass and broadleaved weeds in sugar cane. It possesses the following structure:

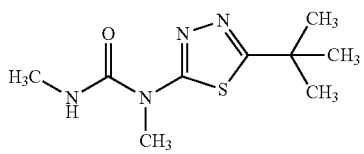

Terbuthylazine is 6-chloro-N-(1,1-dimethylethyl)-N'-ethyl-1,3,5-triazine-2,4-diamine Its herbicidal activity is described in *The Pesticide Manual*, Fifteenth Edition, 2009. Exemplary uses of terbuthylazine include its use for pre and post-emergence weed control, e.g., in maize, sorghum, vines, fruit trees, citrus, coffee, oil palm, cocoa, olives, potatoes, peas, beans, sugarcane, rubber, and forestry (tree nurseries and new plantings). It possesses the following structure:

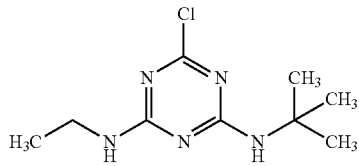

As used herein, herbicide means a compound, e.g., active ingredient that kills, controls or otherwise adversely modifies the growth of plants.

As used herein, a herbicidally effective or vegetation controlling amount is an amount of active ingredient which causes an adversely modifying effect to the vegetation e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, e.g., application to the area adjacent to the vegetation, as well as pre-emergence, post-emergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle, or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Exemplary salts include those derived from alkali or alkaline earth metals and those derived from ammonia and amines Exemplary cations include sodium, potassium, magnesium, and aminium cations of the formula:

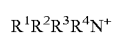

R¹R²R³R⁴N⁺ wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising an herbicidally effective amount of (a) a compound of the formula (I)

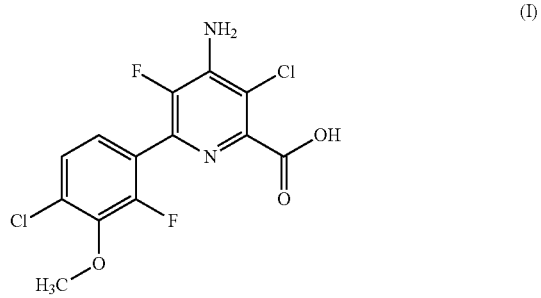 [SMILES: COc1c(Cl)ccc(-c2nc(C(=O)O)c(Cl)c(N)c2F)c1F]

or an agriculturally acceptable salt or ester of thereof, and (b) a PS II inhibitor selected from the group consisting of atrazine, bentazon-sodium, bromoxynil, chlorotoluron, cyanazine, diuron, hexazinone, ioxynil, isoproturon, linuron, methibenzuron, metribuzin, propanil, pyridate, siduron, simazine, simetryne, tebuthiuron and terbuthylazine, or a salt or ester thereof.

Provided herein are also methods of controlling undesirable vegetation comprising contacting the vegetation or the locus thereof, i.e., the area adjacent to the undesirable vegetation, with or applying to the soil or water to prevent the emergence or growth of vegetation a herbicidally effective amount of the compound of formula (I) or agriculturally acceptable salt or ester thereof and (b) a PS II inhibitor selected from the group consisting of atrazine, bentazon-sodium, bromoxynil, chlorotoluron, cyanazine, diuron, hexazinone, ioxynil, isoproturon, linuron, methibenzuron, metribuzin, propanil, pyridate, siduron, simazine, simetryne, tebuthiuron and terbuthylazine, or a salt or ester thereof. In certain embodiments, the methods employ the compositions described herein.

Furthermore, in some embodiments, the combination of compound (I) or agriculturally acceptable salt or ester thereof and a PS II inhibitor or an agriculturally acceptable salt or ester thereof exhibits synergism, e.g., the herbicidal active ingredients are more effective in combination than when applied individually. *The Herbicide Handbook* of the Weed Science Society of America, Ninth Edition, 2007, p. 429 notes that "'synergism' [is] an interaction of two or more factors such that the effect when combined is greater than the predicted effect based on the response of each factor applied separately." In certain embodiments, the compositions exhibit synergy as determined by the Colby's equation. Colby, S. R. 1967. Calculation of the synergistic and antagonistic response of herbicide combinations. Weeds 15:20-22.

In certain embodiments of the compositions and methods described herein, the compound of formula (I), i.e., the carboxylic acid, is employed. In certain embodiments, a carboxylate salt of the compound of formula (I) is employed. In certain embodiments, an aralkyl or alkyl ester is employed. In certain embodiments, a benzyl, substituted benzyl, or $C_{1-4}$ alkyl, e.g., n-butyl ester is employed. In certain embodiments, the benzyl ester is employed.

In some embodiments, the compound of formula (I) or salt or ester thereof and a PS II inhibitor, or an agriculturally acceptable salt or ester thereof are formulated in one composition, tank mixed, applied simultaneously, or applied sequentially.

Herbicidal activity is exhibited by the compounds when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, including but not limited to direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) and rights-of-way (ROW).

In certain embodiments, the compositions and methods provided herein are utilized to control weeds in rice. In certain embodiments, the rice is direct-seeded, water-seeded, or transplanted rice.

The compositions and methods described herein may be used to control undesirable vegetation on glyphosate-tolerant-, 5-enolpyruvylshikimate-3-phosphate (EPSP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenyl-pyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant-, and bromoxynil-tolerant-crops (such as, but not limited to, soybean, cotton, canola/oilseed rape, rice, cereals, corn, sorghum, sunflower, sugar beet, sugarcane, turf, etc.), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, ACCase inhibitors, cyclohexanediones, phenylpyrazolines, imidazolinones, sulfonylureas, pyrimidinylthiobenzoates, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil. The compositions and methods may be used in controlling undesirable vegetation in crops possessing multiple or stacked traits conferring tolerance to multiple chemistries and/or inhibitors of multiple modes of action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix, or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The compositions and methods provided herein are utilized to control undesirable vegetation. Undesirable vegetation includes, but is not limited to, undesirable vegetation that occurs in rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) and rights of way (ROW).

In some embodiments, the methods provided herein are utilized to control undesirable vegetation in rice. In certain embodiments, the undesirable vegetation is *Brachiaria platyphylla* (Groseb.) Nash or *Urochloa platyphylla* (Nash) R. D. Webster (broadleaf signalgrass, BRAPP), *Digitaria sanguinalis* (L.) Scop. (large crabgrass, DIGSA), *Echinochloa* species (ECHSS), *Echinochloa crus-galli* (L.) P. Beauv. (barnyardgrass, ECHCG), *Echinochloa crus-pavonis* (Kunth) Schuh. (gulf cockspur, ECHCV), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Echinochloa phyllopogon* (Stapf) Koso-Pol. (rice barnyardgrass, ECHPO), *Echinochloa polystachya* (Kunth) Hitchc. (creeping river grass, ECHPO), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Oryza* species (red and weedy rice, ORYSS), *Panicum dichotomiflorum* (L.) Michx. (fall panicum, PANDI), *Paspalum dilatatum* Poir. (dallisgrass, PASDI), *Rottboellia cochinchinensis* (Lour.) W. D. Clayton (itchgrass, ROOEX), *Cyperus* species (CYPSS), *Cyperus difformis* L. (smallflower flatsedge, CYPDI), *Cyperus dubius* Rottb. (MAPDU), *Cyperus esculentus* L. (yellow nutsedge, CYPES), *Cyperus iria* L. (rice flatsedge, CYPIR), *Cyperus rotundus* L. (purple nutsedge, CYPRO), *Cyperus serotinus* Rottb./C. B. Clarke (tidalmarsh flatsedge, CYP SE), *Eleocharis* species (ELOSS), *Fimbristylis miliacea* (L.) Vahl (globe fringerush, FIMMI), *Schoenoplectus* species (SCPSS), *Schoenoplectus juncoides* Roxb. (Japanese bulrush, SCPJU), *Bolboschoenus maritimus* (L.) Palla or *Schoenoplectus maritimus* L. Lye (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Commelina benghalensis* L. (Benghal dayflower, COMBE), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea* species (morningglories, IPOSS), *Ipomoea hederacea* (L.) Jacq. (ivyleaf morningglory, IPOHE), *Lindernia dubia* (L.) Pennell (low false pimpernel, LIDDU), *Ludwigia species* (LUDSS), *Ludwigia linifolia* Poir. (southeastern primrose-willow, LUDLI), *Ludwigia octovalvis* (Jacq.) Raven (longfruited primrose-willow, LUDOC), *Monochoria korsakowii* Regel & Maack (monochoria, MOOKA), *Monochoria vaginalis* (Berm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Amaranthus retroflexus* L. (redroot pigweed, AMARE), *Brassica* species (BRSSS), *Chenopodium album* L. (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis species* (SINSS), *Sinapis arvensis* L. (wild mustard, SINAR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, fallowland, IVM and ROW. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Daucus carota* L. (wild carrot, DAUCA), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops, tree and vine crops, and perennial crops. In certain embodiments, the undesirable vegetation is *Alopecurus myosuroides* Huds. (blackgrass, ALOMY), *Avena fatua* L. (wild oat, AVEFA), *Brachiaria decumbens* Stapf. or *Urochloa decumbens* (Stapf) R. D. Webster (Surinam grass, BRADC), *Brachiaria brizantha* (Hochst. ex A. Rich.) Stapf. or *Urochloa brizantha* (Hochst. ex A. Rich.) R. D. (beard grass, BRABR), *Brachiaria platyphylla* (Groseb.) Nash or *Urochloa platyphylla* (Nash) R. D. Webster (broadleaf signalgrass, BRAPP), *Brachiaria plantaginea* (Link) Hitchc. or *Urochloa plantaginea* (Link) R. D. Webster (alexandergrass, BRAPL), *Cenchrus echinatus* L. (southern sandbar, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall *panicum*, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Anoda cristata* (L.) Schlecht. (spurred anoda, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC. or *Spermacoce alata* Aubl. (broadleaf buttonweed, BOILF), *Spermacose latifolia* (broadleaved button weed, BOILF), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Euphorbia hirta* L. or *Chamaesyce hirta* (L.) Millsp. (garden spurge, EPHHI), *Euphorbia dentata* Michx. (toothed spurge, EPHDE), *Erigeron bonariensis* L. or *Conyza bonariensis* (L.) Cronq. (hairy fleabane, ERIBO), *Erigeron canadensis* L. or *Conyza canadensis* (L.) Cronq. (Canadian fleabane, ERICA), *Conyza sumatrensis* (Retz.) E. H. Walker (tall fleabane, ERIFL), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Sida* species (sida, SIDSS), *Sida spinosa* L. (prickly sida, SIDSP), *Sinapis arvensis* L. (wild mustard, SINAR), *Solanum ptychanthum* Dunal (eastern black nightshade, SOLPT), *Tridax procumbens* L. (coat buttons, TRQPR), or *Xanthium strumarium* L. (common cocklebur, XANST).

In some embodiments, the methods provided herein are utilized to control undesirable vegetation in turf. In certain embodiments, the undesirable vegetation is *Bellis perennis* L. (English daisy, BELPE), *Cyperus esculentus* L. (yellow nutsedge, CYPES), *Cyperus* species (CYPSS), *Digitaria sanguinalis* (L.) Scop. (large crabgrass, DIGSA), *Diodia virginiana* L. (Virginia buttonweed, DIQVI), *Euphorbia* species (spurge, EPHSS), *Glechoma hederacea* L. (ground ivy, GLEHE), *Hydrocotyle umbellata* L. (dollarweed, HYDUM), *Kylling a* species (kylling a, KYLSS), *Lamium amplexicaule* L. (henbit, LAMAM), *Murdannia nudiflora* (L.) Brenan (doveweed, MUDNU), *Oxalis* species (woodsorrel, OXASS), *Plantago major* L. (broadleaf plantain, PLAMA), *Plantago lanceolata* L. (buckhorn/narrowleaf plantain, PLALA), *Phyllanthus urinaria* L. (chamberbitter, PYLTE), *Rumex obtusifolius* L. (broadleaf dock, RUMOB), *Stachys floridana* Shuttlew. (Florida betony, STAFL), *Stellaria media* (L.) Vill. (common chickweed, STEME), *Taraxacum officinale* G. H. Weber ex Wiggers (dandelion, TAROF), *Trifolium repens* L. (white clover, TRFRE), or *Viola* species (wild violet, VIOSS).

In some embodiments, the compositions and methods provided herein are utilized to control undesirable vegetation consisting of grass, broadleaf and sedge weeds. In certain embodiments, the compositions and methods provided herein are utilized to control undesirable vegetation including *Abutilon, Amaranthus, Brachiaria, Commelina, Cyperus, Echinochloa, Fimbristylis, Galium, Ipomoea, Kochia, Lamium, Leptochloa, Setaria, Sinapis, Veronica, Xanthium* and *Schoenoplectus* species.

In some embodiments, the combination of compound (I) or agriculturally acceptable ester or salt thereof and a PS II inhibitor or an agriculturally acceptable salt or ester thereof is used to control *Echinochloa crus-galli* (L.) Beauv. (barnyardgrass, ECHCG), *Echinochloa colona* (L.) Link (junglerice, ECHCO), *Ipomoea hederacea* Jacq. (ivyleaf morningglory, IPOHE), *Fimbristylis miliacea* (L.) Vahl (globe fringerush, FIMMI), *Leptochloa chinensis* (L.) Nees (Chinese sprangletop, LEFCH) and *Bolboschoenus maritimus* (L.) Palla or *Schoenoplectus maritimus* (L.) Lye (sea clubrush, SCPMA).

The compounds of formula I or agriculturally acceptable salt or ester thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins, (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors, (e.g., glyphosate), glutamine synthetase inhibitors (e.g., glufosinate, bialafos), microtubule assembly inhibitors, (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

In some embodiments, an agriculturally acceptable ester or salt of bentazon is employed in the methods or compositions described herein. In certain embodiments, the sodium salt of bentazon is employed.

In some embodiments, an agriculturally acceptable ester or salt of ioxynil is employed in the methods or compositions described herein. In certain embodiments, the sodium salt of ioxynil is employed. In certain embodiments, the potassium salt of ioxynil is employed. In certain embodiments, the octanoate ester of ioxynil is employed.

In some embodiments, an agriculturally acceptable ester or salt of bromoxynil is employed in the methods or compositions described herein. In certain embodiments, the potassium salt of bromoxynil is employed. In certain embodiments, the butyl ester of bromoxynil is employed. In certain embodiments, the heptyl ester of bromoxynil is employed. In certain embodiments, the octanoate ester of bromoxynil is employed.

In certain embodiments of the compositions and methods described herein, the compound of formula (I) or salt or ester thereof is used in combination with atrazine or salt thereof. With regard to the compositions, in some embodiments, the weight ratio of the compound of formula (I) or salt or ester thereof to atrazine or salt thereof is within the range from about 1:2200 to about 6:1. In certain embodiments, the weight ratio of the compound of formula (I) or salt or ester thereof to atrazine or salt thereof is within the range from 1:509 to about 1:1. In certain embodiments, the weight ratio of the compound of formula (I) or salt or ester thereof to atrazine or salt thereof is within the range from about 1:512 to about 1:8. In certain embodiments, the weight ratio of the compound of formula (I) or salt or ester thereof to atrazine or salt thereof is within the range from about 1:256 to about 1:16. In certain embodiments, the weight ratio of the compound of formula (I) or salt or ester thereof to atrazine or salt thereof is within the range from about 1:256 to about 1:9. In certain embodiments, the compositions provided herein comprise the compound of formula (I) or its benzyl ester and atrazine or salt thereof. In one embodiment, the composition comprises the compound of formula (I) and atrazine or salt thereof, wherein the weight ratio of the compound of formula (I) to atrazine or salt thereof is about 1:256 to about 1:32. In one embodiment, the composition comprises the benzyl ester of the compound of formula (I) and atrazine or salt thereof, wherein the weight ratio of the benzyl ester of the compound of formula (I) to atrazine or salt thereof is about 1:64 to about 1:16. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 52 grams active ingredient per hectare (g ai/ha) to about 4700 g ai/ha based on the total amount of active ingredients in the composition. In certain embodiments, the composition is applied at an application rate from about 60 grams active ingredient per hectare (g ai/ha) to about 2300 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and atrazine or salt thereof, e.g., sequentially or simultaneously. In some embodiments, the atrazine or salt thereof is applied at a rate from about 50 g ai/ha to about 4400 g ai/ha and the compound of formula (I) of salt or ester thereof is applied at a rate from about 2 g ae/ha to about 300 g ae/ha. In some embodiments, the atrazine or salt thereof is applied at a rate from about 140 g ai/ha to about 2240 g ai/ha and the compound of formula (I) of salt or ester thereof is applied at a rate from about 2 g acid equivalent per hectare (g ae/ha) to about 35 g ae/ha. In some embodiments, the atrazine or salt thereof is applied at a rate from about 280 g ai/ha to about 1120 g ai/ha and the compound of formula (I) of salt or ester thereof is applied at a rate from about 4.38 g acid equivalent per hectare (g ae/ha) to about 17.5 g ae/ha. In certain embodiments, the methods utilize the compound of formula (I), or its benzyl ester and atrazine or salt thereof. In one embodiment, the methods utilize the compound of formula (I) and atrazine or salt thereof, wherein the compound of formula (I) is applied at a rate from about 6.38 g acid equivalent per hectare (g ae/ha) to about 8.75 g ae/ha, and atrazine or salt thereof is applied at a rate of about 280 g ai/ha to about 1120 g ai/ha. In one embodiment, the methods utilize the benzyl ester of the compound of formula (I) and atrazine or salt thereof, wherein the benzyl ester of the compound of formula (I) is applied at a rate from about 4.38 g acid equivalent per hectare (g ae/ha) to about 17.5 g ae/ha, and atrazine or salt thereof is applied at a rate of about 280 g ai/ha to about 560 g ai/ha. In certain embodiments, the methods and compositions utilizing the compound of formula (I) or salt or ester thereof in combination with atrazine or salt thereof are used to control BRAPP, CYPIR, ECHCG, SCPMA, XANST or ECHCO.

In certain embodiments of the compositions and methods described herein, the compound of formula (I) or salt or ester thereof is used in combination with bentazon or salt thereof. With regard to the compositions, in some embodiments, the weight ratio of the compound of formula (I) or salt or ester thereof to bentazon or salt thereof is within the range from about 1:1120 to about 3:1. In certain embodiments, the weight ratio of the compound of formula (I) or salt or ester thereof to bentazon or salt thereof is within the range from about 1:256 to about 1:1.2. In certain embodiments, the weight ratio of the compound of formula (I) or salt or ester thereof to bentazon or salt thereof is within the range from about 1:192 to about 1:3. In certain embodiments, the weight ratio of the compound of formula (I) or salt or ester thereof to is within the range from about 1:96 to about 1:6. In certain embodiments, the compositions provided herein comprise the compound of formula (I) or its benzyl or n-butyl ester and bentazon-sodium. In one embodiment, the composition comprises the compound of formula (I) and bentazon-sodium, wherein the weight ratio of the compound of formula (I) to bentazon-sodium is about 1:96 to about 1:20. In one embodiment, the composition comprises the benzyl ester of the compound of formula (I) and bentazon-sodium, wherein the weight ratio of the benzyl ester of the compound of formula (I) to bentazon-sodium is about 1:96 to about 1:6. In one embodiment, the composition comprises the n-butyl ester of the compound of formula (I) and bentazon-sodium, wherein the weight ratio of the n-butyl ester of the compound of formula (I) to bentazon-sodium is about 1:48 to about 1:16. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 107 grams active ingredient per hectare (g ai/ha) to about 2540 g ai/ha based on the total amount of active ingredients in the composition. In certain embodiments, the composition is applied at an application rate from about 110 grams active ingredient per hectare (g ai/ha) to about 1205 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and bentazon or salt thereof, e.g., sequentially or simultaneously. In some embodiments, the bentazon or salt thereof is applied at a rate from about 105 g ai/ha to about 2240 g ai/ha and the compound of formula (I) of salt or ester thereof is applied at a rate from about 2 g ae/ha to about 300 g ae/ha. In some embodiments, the bentazon or salt thereof is applied at a rate from about 50 g ai/ha to about 2240 g ai/ha and the compound of formula (I) of salt or ester thereof is applied at a rate from about 2 g acid equivalent per hectare (g ae/ha) to about 140 g ae/ha. In some embodiments, the bentazon or salt thereof is applied at a rate from about 105 g ai/ha to about 1120 g ai/ha and the compound of formula (I) of salt or ester thereof is applied at a rate from about 4.38 g acid equivalent per hectare (g ae/ha) to about 70 g ae/ha. In certain embodiments, the methods utilize the compound of formula (I), or its benzyl or n-butyl ester and bentazon-sodium. In one embodiment, the methods utilize the compound of formula (I) and bentazon-sodium, wherein the compound of formula (I) is applied at a rate from about 4.38 g acid equivalent per hectare (g ae/ha) to about 42.4 g ae/ha, and bentazon-sodium is applied at a rate of about 105 g ai/ha to about 1120 g ai/ha. In one embodiment, the methods utilize the benzyl ester of the compound of formula (I) and bentazon-sodium, wherein the benzyl ester of the compound of formula (I) is applied at a rate from about 4.38 g acid equivalent per hectare (g ae/ha) to about 70 g ae/ha, and bentazon-sodium is applied at a rate of about 105 g ai/ha to about 1120 g ai/ha. In one embodiment, the methods utilize the n-butyl ester of the compound of formula (I) and bentazon-sodium, wherein the n-butyl ester of the compound of formula (I) is applied at a rate of about 17.5 g acid equivalent per hectare (g ae/ha) to about 70 g ae/ha, and bentazon-sodium is applied at a rate of about 840 g ai/ha to about 1120 g ai/ha. In certain embodiments, the methods and compositions utilizing the compound of formula (I) or salt or ester thereof in combination with bentazon or salt thereof are used to control ECHCG, ECHOR, IPOHE, LEFCH, or SCPMA.

In certain embodiments of the compositions and methods described herein, the compound of formula (I) or salt or ester thereof is used in combination with bromoxynil or salt thereof. With regard to the compositions, in some embodiments, the weight ratio of the compound of formula (I) or salt or ester thereof to bromoxynil or salt thereof is within the range from about 1:280 to about 12:1. In certain embodiments, the weight ratio of the compound of formula (I) or salt or ester thereof to bromoxynil or salt thereof is within the range from about 1:254 to about 2:1. In certain embodiments, the weight ratio of the compound of formula (I) or salt or ester thereof to bromoxynil or salt thereof is within the range from about 1:18 to about 1:4. In certain embodiments, the compositions comprise the compound of formula (I) or its benzyl or n-butyl ester and bromoxynil or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 27 grams active ingredient per hectare (g ai/ha) to about 3360 g ai/ha based on the total amount of active ingredients in the composition. In certain embodiments, the composition is applied at an application rate from about 50 grams active ingredient per hectare (g ai/ha) to about 610 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and bromoxynil or salt thereof or salt thereof, e.g., sequentially or simultaneously. In some embodiments, the bromoxynil or salt thereof is applied at a rate from about 25 g ai/ha to about 560 g ai/ha and the compound of formula (I) of salt or ester thereof is applied at a rate from about 2 g ae/ha to about 300 g ae/ha. In certain embodiments, the methods utilize the compound of formula (I) or its benzyl or n-butyl ester and bromoxynil or salt thereof can be used to control ECHCG.

In certain embodiments of the compositions and methods described herein, the compound of formula (I) or salt or ester thereof is used in combination with chlorotoluron or salt thereof. With regard to the compositions, in some embodiments, the weight ratio of the compound of formula (I) or salt or ester thereof to chlorotoluron or salt thereof is within the range from about 1:1750 to about 1.5:1. In certain embodiments, the weight ratio of the compound of formula (I) or salt or ester thereof to chlorotoluron or salt thereof is within the range from about 1:909 to about 1:4. In certain embodiments, the compositions comprise the compound of formula (I) or its benzyl or n-butyl ester and chlorotoluron or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 202 grams active ingredient per hectare (g ai/ha) to about 3800 g ai/ha based on the total amount of active ingredients in the composition. In certain embodiments, the composition is applied at an application rate from about 203 grams active ingredient per hectare (g ai/ha) to about 2500 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and chlorotoluron or salt thereof or salt thereof, e.g., sequentially or simultaneously. In some embodiments, the chlorotoluron or salt thereof is applied at a rate from about 200 g ai/ha to about 3500 g ai/ha and the compound of formula (I) of salt or ester thereof is applied at a rate from about 2 g ae/ha to about 300 g ae/ha. In certain embodiments, the methods utilize the compound of formula (I) or its benzyl or n-butyl ester and chlorotoluron or salt thereof.

In certain embodiments of the compositions and methods described herein, the compound of formula (I) salt or ester thereof is used in combination with cyanazine or salt thereof. With regard to the compositions, in some embodiments, the weight ratio of the compound of formula (I) or salt or ester thereof to cyanazine or salt thereof is within the range from about 1:2650 to about 6:1. In certain embodiments, the weight ratio of the compound of formula (I) or salt or ester thereof to cyanazine or salt thereof is within the range from about 1:1600 to about 1:1. In certain embodiments, the weight ratio of the compound of formula (I) or salt or ester thereof to cyanazine or salt thereof is within the range from about 1:110 to about 1:7. In certain embodiments, the compositions comprise the compound of formula (I) or its benzyl or n-butyl ester and cyanazine or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 52 grams active ingredient per hectare (g ai/ha) to about 5600 g ai/ha based on the total amount of active ingredients in the composition. In certain embodiments, the composition is applied at an application rate from about 53 grams active ingredient per hectare (g ai/ha) to about 3550 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and cyanazine or salt thereof, e.g., sequentially or simultaneously. In some embodiments, the cyanazine or salt thereof is applied at a rate from about 50 g ai/ha to about 5300 g ai/ha and the compound of formula (I) of salt or ester thereof is applied at a rate from about 2 g ae/ha to about 300 g ae/ha. In some embodiments, the cyanazine or salt thereof is applied at a rate from about 220 g ai/ha to about 880 g ai/ha and the compound of formula (I) of salt or ester thereof is applied at a rate from about 8 g ae/ha to about 32 g ae/ha. In certain embodiments, the methods utilize the compound of formula (I) or its benzyl or n-butyl ester and cyanazine or salt thereof for the control of BRAPP or IPOHE.

In certain embodiments of the compositions and methods described herein, the compound of formula (I) or salt or ester thereof is used in combination with diuron or salt thereof. With regard to the compositions, in some embodiments, the weight ratio of the compound of formula (I) or salt or ester thereof to diuron or salt thereof is within the range from about 1:3600 to about 6:1. In certain embodiments, the weight ratio of the compound of formula (I) or salt or ester thereof to diuron or salt thereof is within the range from about 1:509 to about 1:1. In certain embodiments, the weight ratio of the compound of formula (I) or salt or ester thereof to diuron or salt thereof is within the range from about 1:70 to about 1:9. In certain embodiments, the compositions comprise the compound of formula (I) or its benzyl or n-butyl ester and diuron or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 52 grams active ingredient per hectare (g ai/ha) to about 7500 g ai/ha based on the total amount of active ingredients in the composition. In certain embodiments, the composition is applied at an application rate from about 55 grams active ingredient per hectare (g ai/ha) to about 2300 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and diuron or salt thereof or salt thereof, e.g., sequentially or simultaneously. In some embodiments, the diuron or salt thereof is applied at a rate from about 50 g ai/ha to about 7200 g ai/ha and the compound of formula (I) of salt or ester thereof is applied at a rate from about 2 g ae/ha to about 300 g ae/ha. In some embodiments, the diuron or salt thereof is applied at a rate from about 280 g ai/ha to about 1,120 g ai/ha and the compound of formula (I) of salt or ester thereof is applied at a rate from about 16 g ae/ha to about 32 g ae/ha. In certain embodiments, the methods utilize the compound of formula (I) or its benzyl or n-butyl ester and diuron or salt thereof for the control of ABUTH, BRAPP, ECHCG, ECHCO, SETFA or SETVI.

In certain embodiments of the compositions and methods described herein, the compound of formula (I) or salt or ester thereof is used in combination with hexazinone or salt thereof. With regard to the compositions, in some embodiments, the weight ratio of the compound of formula (I) or salt or ester thereof to hexazinone or salt thereof is within the range from about 1:200 to about 12:1. In certain embodiments, the weight ratio of the compound of formula (I) or salt or ester thereof to hexazinone or salt thereof is within the range from about 1:1360 to about 2:1. In certain embodiments, the weight ratio of the compound of formula (I) or salt or ester thereof to hexazinone or salt thereof is within the range from about 1:156 to about 1:19. In certain embodiments, the compositions comprise the compound of formula (I) or its benzyl or n-butyl ester and hexazinone or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 27 grams active ingredient per hectare (g ai/ha) to about 5300 g ai/ha based on the total amount of active ingredients in the composition. In certain embodiments, the composition is applied at an application rate from about 28 grams active ingredient per hectare (g ai/ha) to about 3050 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and hexazinone or salt thereof, e.g., sequentially or simultaneously. In some embodiments, the hexazinone or salt thereof is applied at a rate from about 25 g ai/ha to about 5000 g ai/ha and the compound of formula (I) of salt or ester thereof is applied at a rate from about 2 g ae/ha to about 300 g ae/ha. In some embodiments, the hexazinone or salt thereof is applied at a rate from about 625 g ai/ha to about 1,250 g ai/ha and the compound of formula (I) of salt or ester thereof is applied at a rate from about 8 g ae/ha to about 32 g ae/ha. In certain embodiments, the methods utilize the compound of formula (I) or its benzyl or n-butyl ester and hexazinone or salt thereof for the control of ECHCO, ECHCG or IPOHE.

In certain embodiments of the compositions and methods described herein, the compound of formula (I) or salt or ester thereof is used in combination with ioxynil or salt thereof. With regard to the compositions, in some embodiments, the weight ratio of the compound of formula (I) or salt or ester thereof to ioxynil or salt thereof is within the range from about 1:200 to about 12:1. In certain embodiments, the weight ratio of the compound of formula (I) or salt or ester thereof to ioxynil or salt thereof is within the range from about 1:136 to about 6:1. In certain embodiments, the weight ratio of the compound of formula (I) or salt or ester thereof to ioxynil or salt thereof is within the range from about 1:38 to about 1:19. In certain embodiments, the compositions comprise the compound of formula (I) or its benzyl or n-butyl ester and ioxynil or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 27 grams active ingredient per hectare (g ai/ha) to about 700 g ai/ha based on the total amount of active ingredients in the composition. In certain embodiments, the composition is applied at an application rate from about 28 grams active ingredient per hectare (g ai/ha) to about 4500 g ai/ha based on the total amount of active ingredients in the composition. In certain embodiments, the compositions comprise the compound of formula (I) or its benzyl or n-butyl ester and ioxynil or salt thereof. With respect to the methods, in certain embodiments, the methods comprise contacting the undesirable vegetation or locus thereof or applying to the soil or water to prevent the emergence or growth of vegetation a composition described herein. In some embodiments, the ioxynil or salt thereof is applied at a rate from about 25 g ai/ha to about 400 g ai/ha and the compound of formula (I) of salt or ester thereof is applied at a rate from about 2 g ae/ha to about 300 g ae/ha. In some embodiments, the ioxynil or salt thereof is applied at a rate from about 300 g ai/ha to about 400 g ai/ha and the compound of formula (I) of salt or ester thereof is applied at a rate from about 8 g ae/ha to about 32 g ae/ha. In certain embodiments, the methods utilize the compound of formula (I) or its benzyl or n-butyl ester and ioxynil or salt thereof for the control of IPOHE.

In certain embodiments of the compositions and methods described herein, the compound of formula (I) or salt or ester thereof is used in combination with isoproturon or salt thereof. With regard to the compositions, in some embodiments, the weight ratio of the compound of formula (I) or salt or ester thereof to isoproturon or salt thereof is within the range from about 1:750 to about 12:1. In certain embodiments, the weight ratio of the compound of formula (I) or salt or ester thereof to isoproturon or salt thereof is within the range from about 1:600 to about 1:37.5. In certain embodiments, the weight ratio of the compound of formula (I) or salt or ester thereof to isoproturon or salt thereof is within the range from about 1:455 to about 2:1. In certain embodiments, the compositions comprise the compound of formula (I) or its benzyl or n-butyl ester and isoproturon or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 27 grams active ingredient per hectare (g ai/ha) to about 1800 g ai/ha based on the total amount of active ingredients in the composition. In certain embodiments, the composition is applied at an application rate from about 28 grams active ingredient per hectare (g ai/ha) to about 1050 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and isoproturon or salt thereof, e.g., sequentially or simultaneously. In some embodiments, the isoproturon or salt thereof is applied at a rate from about 25 g ai/ha to about 1500 g ai/ha and the compound of formula (I) of salt or ester thereof is applied at a rate from about 2 g ae/ha to about 300 g ae/ha. In some embodiments, the isoproturon or salt thereof is applied at a rate from about 375 g ai/ha to about 1500 g ai/ha and the compound of formula (I) of salt or ester thereof is applied at a rate from about 2.5 g ae/ha to about 10 g ae/ha. In certain embodiments, the methods utilize the compound of formula (I) or its benzyl or n-butyl ester and isoproturon or salt thereof for the control of AMARE, SINAR, GALAP, LAMPU or VERPE.

In certain embodiments of the compositions and methods described herein, the compound of formula (I) or salt or ester thereof is used in combination with linuron or salt thereof. With regard to the compositions, in some embodiments, the weight ratio of the compound of formula (I) or salt or ester thereof to linuron or salt thereof is within the range from about 1:2250 to about 12:1. In certain embodiments, the weight ratio of the compound of formula (I) or salt or ester thereof to linuron or salt thereof is within the range from about 1:39 to about 1:19. In certain embodiments, the weight ratio of the compound of formula (I) or salt or ester thereof to linuron or salt thereof is within the range from about 1:1364 to about 1:1. In certain embodiments, the compositions comprise the compound of formula (I) or its benzyl or n-butyl ester and linuron or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 52 grams active ingredient per hectare (g ai/ha) to about 4800 g ai/ha based on the total amount of active ingredients in the composition. In certain embodiments, the composition is applied at an application rate from about 53 grams active ingredient per hectare (g ai/ha) to about 3050 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and linuron or salt thereof, e.g., sequentially or simultaneously. In some embodiments, the linuron or salt thereof is applied at a rate from about 50 g ai/ha to about 4500 g ai/ha and the compound of formula (I) of salt or ester thereof is applied at a rate from about 2 g ae/ha to about 300 g ae/ha. In some embodiments, the linuron or salt thereof is applied at a rate from about 50 g ai/ha to about 620 g ai/ha and the compound of formula (I) of salt or ester thereof is applied at a rate from about 16 g ae/ha to about 32 g ae/ha. In certain embodiments, the methods utilize the compound of formula (I) or its benzyl or n-butyl ester and linuron or salt thereof for the control of BRAPP.

In certain embodiments of the compositions and methods described herein, the compound of formula (I) or salt or ester thereof is used in combination with methibenzuron or salt thereof. With regard to the compositions, in some embodiments, the weight ratio of the compound of formula (I) or salt or ester thereof to methibenzuron or salt thereof is within the range from about 1:1400 to about 4:1. In certain embodiments, the weight ratio of the compound of formula (I) or salt or ester thereof to methibenzuron or salt thereof is within the range from about 1:909 to about 1:1. In certain embodiments, the compositions comprise the compound of formula (I) or its benzyl or n-butyl ester and methibenzuron or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 72 grams active ingredient per hectare (g ai/ha) to about 3100 g ai/ha based on the total amount of active ingredients in the composition. In certain embodiments, the composition is applied at an application rate from about 73 grams active ingredient per hectare (g ai/ha) to about 2050 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and methibenzuron or salt thereof, e.g., sequentially or simultaneously. In some embodiments, the methibenzuron or salt thereof is applied at a rate from about 70 g ai/ha to about 2800 g ai/ha and the compound of formula (I) of salt or ester thereof is applied at a rate from about 2 g ae/ha to about 300 g ae/ha. In certain embodiments, the methods utilize the compound of formula (I) or its benzyl or n-butyl ester and methibenzuron or salt thereof.

In certain embodiments of the compositions and methods described herein, the compound of formula (I) or salt or ester thereof is used in combination with metribuzin or salt thereof. With regard to the compositions, in some embodiments, the weight ratio of the compound of formula (I) or salt or ester thereof to metribuzin or salt thereof is within the range from about 1:2800 to about 6:1. In certain embodiments, the weight ratio of the compound of formula (I) or salt or ester thereof to metribuzin or salt thereof is within the range from about 1:509 to about 1:1. In certain embodiments, the weight ratio of the compound of formula (I) or salt or ester thereof to metribuzin or salt thereof is within the range from about 1:168 to about 1:1. In certain embodiments, the compositions comprise the compound of formula (I) or its benzyl or n-butyl ester and metribuzin or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 52 grams active ingredient per hectare (g ai/ha) to about 5900 g ai/ha based on the total amount of active ingredients in the composition. In certain embodiments, the composition is applied at an application rate from about 55 grams active ingredient per hectare (g ai/ha) to about 2300 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and metribuzin or salt thereof, e.g., sequentially or simultaneously. In some embodiments, the metribuzin or salt thereof is applied at a rate from about 50 g ai/ha to about 5600 g ai/ha and the compound of formula (I) of salt or ester thereof is applied at a rate from about 2 g ae/ha to about 300 g ae/ha. In some embodiments, the metribuzin or salt thereof is applied at a rate from about 50 g ai/ha to about 420 g ai/ha and the compound of formula (I) of salt or ester thereof is applied at a rate from about 2.5 g ae/ha to about 32 g ae/ha. In certain embodiments, the methods utilize the compound of formula (I) or its benzyl or n-butyl ester and metribuzin or salt thereof for the control of SETFA, KCHSC, LAMPU, SASKR, CHEAL or SINAR.

In certain embodiments of the compositions and methods described herein, the compound of formula (I) or salt or ester thereof is used in combination with propanil or salt thereof. With regard to the compositions, in some embodiments, the weight ratio of the compound of formula (I) or salt or ester thereof to propanil or salt thereof is within the range from about 1:2800 to about 1:1. In certain embodiments, the weight ratio of the compound of formula (I) or salt or ester thereof to propanil or salt thereof is within the range from about 1:767 to about 1:12. In certain embodiments, the weight ratio of the compound of formula (I) or salt or ester thereof to propanil or salt thereof is within the range from about 1:772 to about 1:12. In certain embodiments, the weight ratio of the compound of formula (I) or salt or ester thereof to propanil or salt thereof is within the range from about 1:386 to about 1:24. In certain embodiments, the compositions provided herein comprise the compound of formula (I) or its benzyl or n-butyl ester and propanil. In one embodiment, the composition comprises the compound of formula (I) and propanil, wherein the weight ratio of the compound of formula (I) to propanil is about 1:386 to about 1:48. In one embodiment, the composition comprises the compound of formula (I) and propanil, wherein the weight ratio of the compound of formula (I) to propanil is about 1:763 to about 1:12. In one embodiment, the composition comprises the benzyl ester of the compound of formula (I) and propanil, wherein the weight ratio of the benzyl ester of the compound of formula (I) to propanil is about 1:384 to about 1:24. In one embodiment, the composition comprises the n-butyl ester of the compound of formula (I) and propanil, wherein the weight ratio of the n-butyl ester of the compound of formula (I) to propanil is about 1:210. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 422 grams active ingredient per hectare (g ai/ha) to about 5900 g ai/ha based on the total amount of active ingredients in the composition. In certain embodiments, the composition is applied at an application rate from about 425 grams active ingredient per hectare (g ai/ha) to about 3400 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and propanil or salt thereof, e.g., sequentially or simultaneously. In some embodiments, the propanil or salt thereof is applied at a rate from about 420 g ai/ha to about 5600 g ai/ha and the compound of formula (I) of salt or ester thereof is applied at a rate from about 2 g ae/ha to about 300 g ae/ha. In some embodiments, the propanil or salt thereof is applied at a rate from about 210 g ai/ha to about 6720 g ai/ha and the compound of formula (I) of salt or ester thereof is applied at a rate from about 2 g acid equivalent per hectare (g ae/ha) to about 70 g ae/ha. In some embodiments, the propanil or salt thereof is applied at a rate from about 420 g ai/ha to about 3360 g ai/ha and the compound of formula (I) of salt or ester thereof is applied at a rate from about 4 g acid equivalent per hectare (g ae/ha) to about 35 g ae/ha. In some embodiments, the propanil or salt thereof is applied at a rate from about 420 g ai/ha to about 3360 g ai/ha and the compound of formula (I) of salt or ester thereof is applied at a rate from about 4.38 g acid equivalent per hectare (g ae/ha) to about 35 g ae/ha. In certain embodiments, the methods utilize the compound of formula (I), or its benzyl or n-butyl ester and propanil. In one embodiment, the methods utilize the compound of formula (I) and propanil, wherein the compound of formula (I) is applied at a rate from about 4.38 g acid equivalent per hectare (g ae/ha) to about 35 g ae/ha, and propanil is applied at a rate of about 420 g ai/ha to about 3360 g ai/ha. In one embodiment, the methods utilize the benzyl ester of the compound of formula (I) and propanil, wherein the benzyl ester of the compound of formula (I) is applied at a rate from about 4.38 g acid equivalent per hectare (g ae/ha) to about 35 g ae/ha, and propanil is applied at a rate of about 420 g ai/ha to about 3360 g ai/ha. In one embodiment, the methods utilize the n-butyl ester of the compound of formula (I) and propanil, wherein the n-butyl ester of the compound of formula (I) is applied at a rate of about 32 g acid equivalent per hectare (g ae/ha), and propanil is applied at a rate of about 3360 g ai/ha. In certain embodiments, the methods and compositions utilizing the compound of formula (I) or salt or ester thereof in combination with propanil are used to control ECHCG, ECHCO, COMBE, IPOHE, or SCPMA.

In certain embodiments of the compositions and methods described herein, the compound of formula (I) or salt or ester thereof is used in combination with pyridate. With regard to the compositions, in some embodiments, the weight ratio of the compound of formula (I) or salt or ester thereof to pyridate is within the range from about 1:800 to about 12:1. In certain embodiments, the weight ratio of the compound of formula (I) or salt or ester thereof to pyridate is within the range from about 1:545 to about 6:1. In certain embodiments, the compositions comprise the compound of formula (I) or its benzyl or n-butyl ester and pyridate. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 27 grams active ingredient per hectare (g ai/ha) to about 1800 g ai/ha based on the total amount of active ingredients in the composition. In certain embodiments, the composition is applied at an application rate from about 28 grams active ingredient per hectare (g ai/ha) to about 1350 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pyridate, e.g., sequentially or simultaneously. In some embodiments, the pyridate is applied at a rate from about 25 g ai/ha to about 1600 g ai/ha and the compound of formula (I) of salt or ester thereof is applied at a rate from about 2 g ae/ha to about 300 g ae/ha. In certain embodiments, the methods utilize the compound of formula (I) or its benzyl or n-butyl ester and pyridate.

In certain embodiments of the compositions and methods described herein, the compound of formula (I) or salt or ester thereof is used in combination with siduron or salt thereof. With regard to the compositions, in some embodiments, the weight ratio of the compound of formula (I) or salt or ester thereof to siduron or salt thereof is within the range from about 1:4500 to about 2:1. In certain embodiments, the weight ratio of the compound of formula (I) or salt or ester thereof to siduron or salt thereof is within the range from about 1:2728 to about 1:3. In certain embodiments, the compositions comprise the compound of formula (I) or its benzyl or n-butyl ester and siduron or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 142 grams active ingredient per hectare (g ai/ha) to about 9300 g ai/ha based on the total amount of active ingredients in the composition. In certain embodiments, the composition is applied at an application rate from about 143 grams active ingredient per hectare (g ai/ha) to about 6050 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and siduron or salt thereof, e.g., sequentially or simultaneously. In some embodiments, the siduron or salt thereof is applied at a rate from about 140 g ai/ha to about 9000 g ai/ha and the compound of formula (I) of salt or ester thereof is applied at a rate from about 2 g ae/ha to about 300 g ae/ha. In certain embodiments, the methods utilize the compound of formula (I) or its benzyl or n-butyl ester and siduron or salt thereof.

In certain embodiments of the compositions and methods described herein, the compound of formula (I) or salt or ester thereof is used in combination with simazine or salt thereof. With regard to the compositions, in some embodiments, the weight ratio of the compound of formula (I) or salt or ester thereof to simazine or salt thereof is within the range from about 1:4250 to about 2:1. In certain embodiments, the weight ratio of the compound of formula (I) or salt or ester thereof to simazine or salt thereof is within the range from about 1:2728 to about 1:3. In certain embodiments, the weight ratio of the compound of formula (I) or salt or ester thereof to simazine or salt thereof is within the range from about 1:280 to about 1:17.5. In certain embodiments, the compositions comprise the compound of formula (I) or its benzyl or n-butyl ester and simazine or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 142 grams active ingredient per hectare (g ai/ha) to about 8800 g ai/ha based on the total amount of active ingredients in the composition. In certain embodiments, the composition is applied at an application rate from about 143 grams active ingredient per hectare (g ai/ha) to about 6050 g ai/ha based on the total amount of active ingredients in the composition. In certain embodiments, the composition is applied at an application rate from about 568 grams active ingredient per hectare (g ai/ha) to about 2272 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and simazine or salt thereof, e.g., sequentially or simultaneously. In some embodiments, the simazine or salt thereof is applied at a rate from about 140 g ai/ha to about 8500 g ai/ha and the compound of formula (I) of salt or ester thereof is applied at a rate from about 2 g ae/ha to about 300 g ae/ha. In some embodiments, the simazine or salt thereof is applied at a rate from about 560 g ai/ha to about 2240 g ai/ha and the compound of formula (I) of salt or ester thereof is applied at a rate from about 8 g ae/ha to about 32 g ae/ha. In certain embodiments, the methods utilize the compound of formula (I) or its benzyl or n-butyl ester and simazine or salt thereof for the control of BRAPP, ECHCG, ECHCO, CYPIR or XANST.

In certain embodiments of the compositions and methods described herein, the compound of formula (I) or salt or ester thereof is used in combination with simetryne or salt thereof. With regard to the compositions, in some embodiments, the weight ratio of the compound of formula (I) or salt or ester thereof to simetryne or salt thereof is within the range from about 1:1000 to about 12:1. In certain embodiments, the weight ratio of the compound of formula (I) or salt or ester thereof to simetryne or salt thereof is within the range from about 1:682 to about 6:1. In certain embodiments, the weight ratio of the compound of formula (I) or salt or ester thereof to simetryne or salt thereof is within the range from about 1:56 to about 1:3.5. In certain embodiments, the compositions comprise the compound of formula (I) or its benzyl or n-butyl ester and simetryne or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 27 grams active ingredient per hectare (g ai/ha) to about 2300 g ai/ha based on the total amount of active ingredients in the composition. In certain embodiments, the composition is applied at an application rate from about 28 grams active ingredient per hectare (g ai/ha) to about 1650 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and simetryne or salt thereof, e.g., sequentially or simultaneously. In some embodiments, the simetryne or salt thereof is applied at a rate from about 25 g ai/ha to about 2000 g ai/ha and the compound of formula (I) of salt or ester thereof is applied at a rate from about 2 g ae/ha to about 300 g ae/ha. In some embodiments, the simetryne or salt thereof is applied at a rate from about 110 g ai/ha to about 450 g ai/ha and the compound of formula (I) of salt or ester thereof is applied at a rate from about 8 g ae/ha to about 32 g ae/ha. In certain embodiments, the methods utilize the compound of formula (I) or its benzyl or n-butyl ester and simetryne or salt thereof for the control of ECHCO, ECHOR, CYPIR, CYPRO, FIMMI or LEFCH.

In certain embodiments of the compositions and methods described herein, the compound of formula (I) or salt or ester thereof is used in combination with tebuthiuron or salt thereof. With regard to the compositions, in some embodiments, the weight ratio of the compound of formula (I) or salt or ester thereof to tebuthiuron or salt thereof is within the range from about 1:2240 to about 2:1. In certain embodiments, the weight ratio of the compound of formula (I) or salt or ester thereof to tebuthiuron or salt thereof is within the range from about 1:1818 to about 1:1. In certain embodiments, the weight ratio of the compound of formula (I) or salt or ester thereof to tebuthiuron or salt thereof is within the range from about 1:420 to about 1:6.5. In certain embodiments, the compositions comprise the compound of formula (I) or its benzyl or n-butyl ester and tebuthiuron or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 142 grams active ingredient per hectare (g ai/ha) to about 4780 g ai/ha based on the total amount of active ingredients in the composition. In certain embodiments, the composition is applied at an application rate from about 143 grams active ingredient per hectare (g ai/ha) to about 4100 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and tebuthiuron or salt thereof, e.g., sequentially or simultaneously. In some embodiments, the tebuthiuron or salt thereof is applied at a rate from about 140 g ai/ha to about 4480 g ai/ha and the compound of formula (I) of salt or ester thereof is applied at a rate from about 2 g ae/ha to about 300 g ae/ha. In some embodiments, the tebuthiuron or salt thereof is applied at a rate from about 210 g ai/ha to about 3360 g ai/ha and the compound of formula (I) of salt or ester thereof is applied at a rate from about 8 g ae/ha to about 32 g ae/ha. In certain embodiments, the methods utilize the compound of formula (I) or its benzyl or n-butyl ester and tebuthiuron or salt thereof for the control of IPOHE, or XANST.

In certain embodiments of the compositions and methods described herein, the compound of formula (I) or salt or ester thereof is used in combination with terbuthylazine or salt thereof. With regard to the compositions, in some embodiments, the weight ratio of the compound of formula (I) or salt or ester thereof to terbuthylazine or salt thereof is within the range from about 1:1500 to about 3:1. In certain embodiments, the weight ratio of the compound of formula (I) or salt or ester thereof to terbuthylazine or salt thereof is within the range from about 1:1018 to about 1:2.5. In certain embodiments, the weight ratio of the compound of formula (I) or salt or ester thereof to terbuthylazine or salt thereof is within the range from about 1:62 to about 1:31. In certain embodiments, the compositions comprise the compound of formula (I) or its benzyl or n-butyl ester and terbuthylazine or salt thereof. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 127 grams active ingredient per hectare (g ai/ha) to about 3300 g ai/ha based on the total amount of active ingredients in the composition. In certain embodiments, the composition is applied at an application rate from about 128 grams active ingredient per hectare (g ai/ha) to about 2290 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and terbuthylazine or salt thereof, e.g., sequentially or simultaneously. In some embodiments, the terbuthylazine or salt thereof is applied at a rate from about 125 g ai/ha to about 3000 g ai/ha and the compound of formula (I) of salt or ester thereof is applied at a rate from about 2 g ae/ha to about 300 g ae/ha. In some embodiments, the terbuthylazine or salt thereof is applied at a rate from about 125 g ai/ha to about 1000 g ai/ha and the compound of formula (I) of salt or ester thereof is applied at a rate from about 16 g ae/ha to about 32 g ae/ha. In certain embodiments, the methods utilize the compound of formula (I) or its benzyl or n-butyl ester and terbuthylazine or salt thereof for the control of XANST.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA; 4-CPB; 4-CPP; 2,4-D; 2,4-D choline salt, 2,4-D esters and amines, 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, azafenidin, azimsulfuron, aziprotryne, barban, BCPC, beflubutamid, benazolin, bencarbazone, benfluralin, benfuresate, bensulfuron-methyl, bensulide, benthiocarb, benzadox, benzfendizone, benzipram, benzobicyclon, benzofenap, benzofluor, benzoylprop, benzthiazuron, bialaphos, bicyclopyrone, bifenox, bilanafos, bispyribac-sodium, borax, bromacil, bromobonil, bromobutide, bromofenoxim, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyclopyrimorate, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofopmethyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, fluoroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate, halauxifen, halauxifen-methyl, halosafen, halosulfuron-methyl, haloxydine, haloxyfop-methyl, haloxyfop-P-methyl, hexachloroacetone, hexaflurate, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ipazine, ipfencarbazone, iprymidam, isocarbamid, isocil, isomethiozin, isonoruron, isopolinate, isopropalin, isouron, isoxaben, isoxachlortole, isoxaflutole, isoxapyrifop, karbutilate, ketospiradox, lactofen, lenacil, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, orthodichlorobenzene, orthosulfamuron, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, simeton, SMA, sodium arsenite, sodium azide, sodium chlorate, sulcotrione, sulfallate, sulfentrazone, sulfometuron, sulfosate, sulfosulfuron, sulfuric acid, sulglycapin, swep, SYN-523, TCA, tebutam, tefuryltrione, tembotrione, tepraloxydim, terbacil, terbucarb, terbuchlor, terbumeton, terbutryn, tetrafluoron, thenylchlor, thiazafluoron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The compositions and methods described herein, can further be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, EPSP synthase inhibitor-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS-tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, and bromoxynil-tolerant crops, and crops possessing multiple or stacked traits conferring tolerance to multiple chemistries and/or multiple modes of action via single and/or multiple resistance mechanisms. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix, or as a sequential application.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, ethephon, pentachlorophenol, thidiazuron, tribufos, aviglycine, gibberellins, gibberellic acid, abscisic acid, ancymidol, fosamine, glyphosine, isopyrimol, jasmonic acid, maleic hydrazide, mepiquat, 2,3,5-tri-iodobenzoic acid, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol and trinexapac.

In some embodiments, the plant growth regulators are employed in one or more crops or settings, such as rice, cereal crops, corn, maize, broadleaf crops, oilseed rape/canola, turf, pineapple, sugarcane, sunflower, pastures, grasslands, rangelands, fallowland, turf, tree and vine orchards, plantation crops, vegetables, and non-crop (ornamentals) settings. In some embodiments, the plant growth regulator is mixed with the compound of formula (I), or mixed with the compound of formula (I) and PSII inhibitors to cause a preferentially advantageous effect on plants.

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG (400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, Water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from 0.0005 to 98 percent by weight. In some embodiments, the concentration is from 0.0006 to 90 percent by weight. In compositions designed to be employed as concentrates, the active ingredients, in certain embodiments, are present in a concentration from 0.1 to 98 weight percent, and in certain embodiments 0.2 to 90 weight percent. Such compositions are, in certain embodiments, diluted with an inert carrier, such as water, before application. The diluted compositions usually applied to weeds or the locus of weeds contain, in certain embodiments, 0.0052 to 25.0 weight percent active ingredient and in certain embodiments contain 0.01 to 15 weight percent active ingredient.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Results in Examples I, II, III, and IV are greenhouse trial results.

Example I

Evaluation of Postemergence Foliar-Applied Herbicidal Mixtures for Weed Control in Direct Seeded Rice Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a volume of 1 quart and a surface area of 83.6 square centimeters ($cm^2$). When required to ensure good germination and healthy plants, a fungicide treatment and/or other chemical or physical treatment was applied. The plants were grown for 8-22 days in a greenhouse with an approximate 14 h photoperiod which was maintained at about 29° C. during the day and 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (Compound A), each formulated as an SC (suspension concentrate), and various herbicidal components alone and in combination. Forms of compound A were applied on an acid equivalent basis.

Forms of compound A (compound of formula I) tested include:

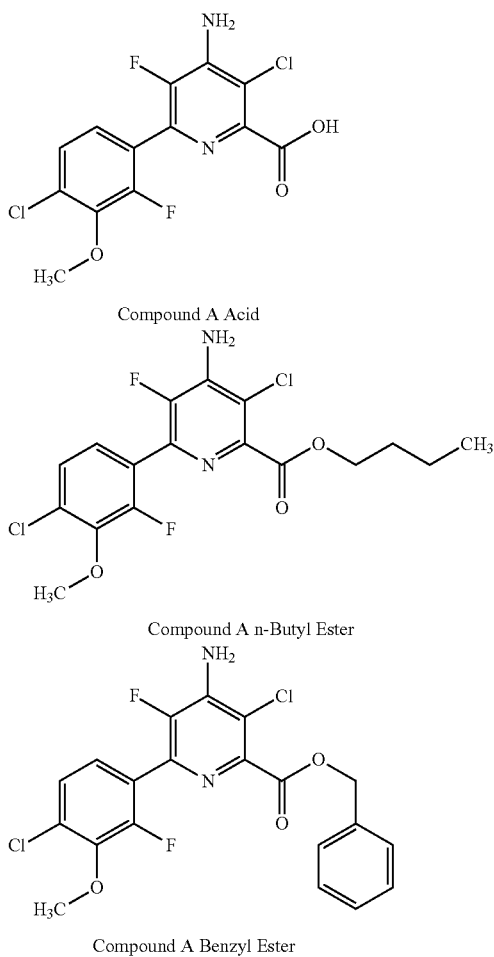

Compound A Acid

Compound A n-Butyl Ester

Compound A Benzyl Ester

Other herbicidal components were applied on an active ingredient basis and included Photosystem II (PSII)-inhibiting herbicides propanil formulated as Stam® M4 EC, bentazon-sodium formulated as Basagran®, atrazine formulated as Atrazine 90 WDG, bromoxynil octanoate ester formulated as Buctril®, simetryne (technical grade material), simazine formulated as Princep® Caliber 90, ioxynil (technical grade material), cyanazine (technical grade material), and hexazinone (technical grade material).

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrated to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) crop oil concentrate so that the final spray solutions contained 1.25+/−0.05% (v/v) crop oil concentrate.

For treatments comprised of technical compounds, weighed amounts can be placed individually in 25 mL glass vials and dissolved in a volume of 97:3 v/v acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) crop oil concentrate so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials were placed individually in 25 mL glass vials and dissolved in a volume of 97:3 v/v acetone/DMSO to obtain 12× stock solutions, and measured amounts of the formulated compounds were placed individually in 25 mL glass vials and diluted in a volume of 1.5% (v/v) crop oil concentrate or water to obtain 12× stock solutions. If a test compound did not dissolve readily, the mixture was warmed and/or sonicated. Application solutions were prepared by adding an appropriate amount of each stock solution (eg, 1 mL) and diluted to the appropriate final concentrations with the addition of an appropriate amount of an aqueous mixture of 1.5% (v/v) crop oil concentrate so that the final spray solutions contained 1.25% (v/v) crop oil concentrate. As required, additional water and/or 97:3 v/v acetone/DMSO was added to individual application solutions so that the final acetone and DMSO concentrations of the application solutions being compared were 8.1% and 0.25%, respectively.

All stock solutions and applications solutions were visually inspected for compound compatibility prior to application. Spray solutions were applied to the plant material with an overhead Mandel track sprayer equipped with a 8002E nozzles calibrated to deliver 187 L/ha over an application area of 0.503 m$^2$ at a spray height of 18 to 20 inches (46 to 50 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

Expected=$A+B-(A \times B/100)$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 1-14.

TABLE 1

Synergistic Activity of Foliar-Applied Compound A Acid and Propanil Herbicidal Compositions on Weed Control in a Rice Cropping System.

| Compound | | Visual Weed Control (%)-21 DAA | | | | | |
|---|---|---|---|---|---|---|---|
| A Acid | Propanil | ECHCG | | ECHCO | | IPOHE | |
| g ae/ha | g ai/ha | Obs | Exp | Obs | Exp | Obs | Exp |
| 4.38 | 0 | 33 | — | 43 | — | 15 | — |
| 8.75 | 0 | 55 | — | 63 | — | 35 | — |
| 0 | 420 | 10 | — | 10 | — | 0 | — |
| 0 | 840 | 10 | — | 25 | — | 0 | — |
| 0 | 1680 | 40 | — | 25 | — | 0 | — |
| 4.38 | 420 | 90 | 39 | 75 | 48 | 25 | 15 |
| 8.75 | 420 | 95 | 60 | 85 | 66 | 50 | 35 |
| 4.38 | 840 | 90 | 39 | 75 | 57 | 50 | 15 |
| 8.75 | 840 | 95 | 60 | 90 | 72 | 65 | 35 |
| 4.38 | 1680 | 95 | 60 | 90 | 57 | 60 | 15 |
| 8.75 | 1680 | 95 | 73 | 100 | 72 | 55 | 35 |

| Compound | | Visual Weed Control (%)-20 DAA | |
|---|---|---|---|
| A Acid | Propanil | IPOHE | |
| g ae/ha | g ai/ha | Obs | Exp |
| 19.4 | 0 | 15 | — |
| 0 | 3360 | 40 | — |
| 19.4 | 3360 | 73 | 49 |

TABLE 2

Synergistic Activity of Foliar-Applied Compound A Benzyl Ester and Propanil Herbicidal Compositions on Weed Control in a Rice Cropping System.

| Compound | | Visual Weed Control (%)-21 DAA | | | | | |
|---|---|---|---|---|---|---|---|
| A Benzyl Ester | Propanil | ECHCG | | ECHCO | | IPOHE | |
| g ae/ha | g ai/ha | Obs | Exp | Obs | Exp | Obs | Exp |
| 4.38 | 0 | 48 | — | 60 | — | 0 | — |
| 8.75 | 0 | 55 | — | 68 | — | 15 | — |
| 17.5 | 0 | 85 | — | 83 | — | 38 | — |
| 0 | 420 | 10 | — | 10 | — | 0 | — |
| 0 | 840 | 10 | — | 25 | — | 0 | — |
| 0 | 1680 | 40 | — | 25 | — | 0 | — |
| 4.38 | 420 | 60 | 53 | 75 | 64 | 15 | 0 |
| 8.75 | 420 | 90 | 60 | 90 | 71 | 50 | 15 |
| 17.5 | 420 | 95 | 87 | 95 | 84 | 60 | 38 |
| 4.38 | 840 | 90 | 53 | 85 | 70 | 20 | 0 |
| 8.75 | 840 | 95 | 60 | 80 | 76 | 35 | 15 |
| 17.5 | 840 | 95 | 87 | 99 | 87 | 65 | 38 |
| 4.38 | 1680 | 70 | 69 | 100 | 70 | 50 | 0 |
| 8.75 | 1680 | 90 | 73 | 100 | 76 | 50 | 15 |
| 17.5 | 1680 | 95 | 91 | 100 | 87 | 65 | 38 |

| Compound | | Visual Weed Control (%)-20 DAA | |
|---|---|---|---|
| A Benzyl Ester | Propanil | IPOHE | |
| g ae/ha | g ai/ha | Obs | Exp |
| 16 | 0 | 18 | — |
| 0 | 3360 | 40 | — |
| 16 | 3360 | 85 | 51 |

TABLE 2-continued

Synergistic Activity of Foliar-Applied Compound A Benzyl Ester and Propanil Herbicidal Compositions on Weed Control in a Rice Cropping System.

| Compound | | Visual Weed Control (%)-20 DAA | |
|---|---|---|---|
| A Benzyl Ester | Propanil | COMBE | |
| g ae/ha | g ai/ha | Obs | Exp |
| 6 | 0 | 80 | — |
| 24 | 0 | 0 | — |
| 0 | 3360 | 10 | — |
| 6 | 3360 | 80 | 80 |
| 24 | 3360 | 95 | 82 |

TABLE 3

Synergistic Activity of Foliar-Applied Compound A n-Butyl Ester and Propanil Herbicidal Compositions on Weed Control in a Rice Cropping System.

| Compound | | Visual Weed Control (%) - 20 DAA | |
|---|---|---|---|
| A n-Butyl Ester | Propanil | IPOHE | |
| g ae/ha | g ai/ha | Obs | Exp |
| 16 | 0 | 15 | — |
| 0 | 3360 | 40 | — |
| 16 | 3360 | 70 | 49 |

TABLE 4

Synergistic Activity of Foliar-Applied Compound A Acid and Bentazon-sodium Herbicidal Compositions on Weed Control in a Rice Cropping System.

| Compound | | Visual Weed Control (%) - 21 DAA | |
|---|---|---|---|
| A Acid | Bentazon-sodium | IPOHE | |
| g ae/ha | g ai/ha | Obs | Exp |
| 4.38 | 0 | 15 | — |
| 0 | 105 | 0 | — |
| 0 | 210 | 0 | — |
| 0 | 420 | 10 | — |
| 4.38 | 105 | 30 | 15 |
| 4.38 | 210 | 60 | 15 |
| 4.38 | 420 | 50 | 24 |

| Compound | | Visual Weed Control (%) - 20 DAA | |
|---|---|---|---|
| A Acid | Bentazon-sodium | IPOHE | |
| g ae/ha | g ae/ha | Obs | Exp |
| 21.2 | 0 | 35 | — |
| 42.4 | 0 | 55 | — |
| 0 | 840 | 13 | — |
| 21.2 | 840 | 73 | 43 |
| 42.4 | 840 | 80 | 61 |

TABLE 5

Synergistic Activity of Foliar-Applied Compound A Benzyl Ester and Bentazon-sodium Herbicidal Compositions on Weed Control in a Rice Cropping System.

| Compound A Benzyl Ester | Bentazon-sodium | Visual Weed Control (%) - 21 DAA IPOHE | |
|---|---|---|---|
| g ae/ha | g ai/ha | Obs | Exp |
| 4.38 | 0 | 0 | — |
| 8.75 | 0 | 15 | — |
| 17.5 | 0 | 38 | — |
| 0 | 105 | 0 | — |
| 0 | 210 | 0 | — |
| 0 | 420 | 10 | — |
| 4.38 | 105 | 40 | 0 |
| 8.75 | 105 | 65 | 15 |
| 17.5 | 105 | 60 | 38 |
| 4.38 | 210 | 30 | 0 |
| 8.75 | 210 | 40 | 15 |
| 17.5 | 210 | 65 | 38 |
| 4.38 | 420 | 30 | 10 |
| 8.75 | 420 | 60 | 24 |
| 17.5 | 420 | 65 | 44 |
| 17.5 | 0 | 38 | — |
| 35 | 0 | 55 | — |
| 0 | 840 | 13 | — |
| 17.5 | 840 | 60 | 45 |
| 35 | 840 | 78 | 61 |

| Compound A Benzyl Ester | Bentazon sodium | Visual Weed Control (%) - 20 DAA COMBE | |
|---|---|---|---|
| g ae/ha | g ai/ha | Obs | Exp |
| 6 | 0 | 70 | — |
| 24 | 0 | 80 | — |
| 0 | 280 | 10 | — |
| 6 | 280 | 75 | 73 |
| 24 | 280 | 95 | 82 |

TABLE 6

Synergistic Activity of Foliar-Applied Compound A n-Butyl Ester and Bentazon-sodium Herbicidal Compositions on Weed Control in a Rice Cropping System.

| Compound A n-Butyl Ester | Bentazon-sodium | Visual Weed Control (%) - 20 DAA IPOHE | |
|---|---|---|---|
| g ae/ha | g ae/ha | Obs | Exp |
| 17.5 | 0 | 48 | — |
| 0 | 840 | 13 | — |
| 17.5 | 840 | 85 | 54 |

TABLE 7

Synergistic Activity of Foliar-Applied Compound A Acid and Atrazine Herbicidal Compositions on Control of Weeds Common to Rice Cropping Systems.

| Compound A Acid | Atrazine | Visual Weed Control (%)-22 DAA BRAPP | |
|---|---|---|---|
| g ae/ha | g ai/ha | Obs | Exp |
| 4.38 | 0 | 45 | — |
| 8.75 | 0 | 70 | — |
| 0 | 280 | 0 | — |
| 0 | 560 | 0 | — |
| 4.38 | 280 | 60 | 45 |
| 8.75 | 280 | 85 | 70 |
| 4.38 | 560 | 70 | 45 |
| 8.75 | 560 | 75 | 70 |

| Compound A Acid | Atrazine | Visual Weed Control (%)-22 DAA | | | | | |
|---|---|---|---|---|---|---|---|
| | | ECHCG | | ECHCO | | CYPIR | |
| g ae/ha | g ai/ha | Obs | Exp | Obs | Exp | Obs | Exp |
| 4.38 | 0 | 20 | — | 20 | — | 15 | — |
| 0 | 280 | 0 | — | 10 | — | 0 | — |
| 0 | 560 | 20 | — | 10 | — | 100 | — |
| 0 | 1120 | 70 | — | 60 | — | 80 | — |
| 4.38 | 280 | 50 | 20 | 50 | 28 | 100 | 15 |
| 4.38 | 560 | 80 | 36 | 70 | 28 | 100 | 100 |
| 4.38 | 1120 | 100 | 76 | 99 | 68 | 100 | 83 |

TABLE 8

Synergistic Activity of Foliar-Applied Compound A Benzyl Ester and Atrazine Herbicidal Compositions on Control of Weeds Common to Rice Cropping Systems.

| Compound A Benzyl Ester | Atrazine | Visual Weed Control (%) - 22 DAA BRAPP | |
|---|---|---|---|
| g ae/ha | g ai/ha | Obs | Exp |
| 4.38 | 0 | 55 | — |
| 8.75 | 0 | 70 | — |
| 17.5 | 0 | 75 | — |
| 0 | 280 | 0 | — |
| 0 | 560 | 0 | — |
| 4.38 | 280 | 55 | 55 |
| 8.75 | 280 | 80 | 70 |
| 17.5 | 280 | 85 | 75 |
| 4.38 | 560 | 65 | 55 |
| 8.75 | 560 | 85 | 70 |
| 17.5 | 560 | 95 | 75 |

TABLE 9

Synergistic Activity of Foliar-Applied Compound A Benzyl Ester and Bromoxynil Herbicidal Compositions on Control of Weeds Common to Rice Cropping Systems.

| Compound A Benzyl Ester | Bromoxynil Octanoate Ester | Visual Weed Control (%) - 22 DAA ECHCG | |
|---|---|---|---|
| g ae/ha | g ai/ha | Obs | Exp |
| 8 | 0 | 35 | — |
| 16 | 0 | 65 | — |
| 32 | 0 | 80 | — |
| 0 | 140 | 0 | — |
| 8 | 140 | 50 | 35 |
| 16 | 140 | 80 | 65 |
| 32 | 140 | 90 | 80 |

TABLE 10

Synergistic Activity of Foliar-Applied Compound A Benzyl Ester and Simetryne Herbicidal Compositions on Control of Weeds Common to Rice Cropping Systems.

| Compound A Benzyl Ester | Simetryne | Visual Weed Control (%) - 21 DAA ECHCO | |
|---|---|---|---|
| g ae/ha | g ai/ha | Obs | Exp |
| 8 | 0 | 75 | — |
| 16 | 0 | 85 | — |
| 32 | 0 | 95 | — |
| 0 | 450 | 45 | — |
| 8 | 450 | 100 | 86 |
| 16 | 450 | 95 | 92 |
| 32 | 450 | 100 | 97 |

| Compound A Benzyl Ester | Simetryne | Visual Weed Control (%) - 22 DAA LEFCH | |
|---|---|---|---|
| g ae/ha | g ai/ha | Obs | Exp |
| 8 | 0 | 35 | — |
| 16 | 0 | 40 | — |
| 0 | 225 | 40 | — |
| 8 | 225 | 80 | 61 |
| 16 | 225 | 70 | 64 |

| Compound A Benzyl Ester | Simetryne | Visual Weed Control (%) - 22 DAA CYPIR | |
|---|---|---|---|
| g ae/ha | g ai/ha | Obs | Exp |
| 8 | 0 | 10 | — |
| 16 | 0 | 60 | — |
| 0 | 112.5 | 0 | — |
| 0 | 225 | 0 | — |
| 0 | 450 | 30 | — |
| 8 | 112.5 | 100 | 10 |
| 16 | 112.5 | 90 | 60 |
| 8 | 225 | 60 | 10 |
| 16 | 225 | 100 | 60 |
| 8 | 450 | 100 | 37 |
| 16 | 450 | 100 | 72 |

TABLE 11

Synergistic Activity of Foliar-Applied Compound A Benzyl Ester and Simazine Herbicidal Compositions on Control of Weeds Common to Rice Cropping Systems.

| Compound A Benzyl Ester | Simazine | Visual Weed Control (%)-20 DAA | | | | | | | |
|---|---|---|---|---|---|---|---|---|---|
| | | BRAPP | | ECHCG | | ECHCO | | CYPIR | |
| g ae/ha | g ai/ha | Obs | Exp | Obs | Exp | Obs | Exp | Obs | Exp |
| 8 | 0 | 55 | — | 70 | — | 65 | — | 70 | — |
| 16 | 0 | 90 | — | 90 | — | 85 | — | 90 | — |
| 32 | 0 | 90 | — | 90 | — | 95 | — | 90 | — |
| 0 | 560 | 0 | — | 0 | — | 0 | — | 0 | — |
| 0 | 1120 | 0 | — | 0 | — | 0 | — | 0 | — |
| 0 | 2240 | 0 | — | 0 | — | 0 | — | 30 | — |
| 8 | 560 | 80 | 55 | 95 | 70 | 80 | 65 | 100 | 70 |
| 16 | 560 | 90 | 90 | 95 | 90 | 85 | 85 | 85 | 90 |
| 32 | 560 | 95 | 90 | 99 | 90 | 95 | 95 | 100 | 90 |
| 8 | 1120 | 80 | 55 | 85 | 70 | 75 | 65 | 100 | 70 |
| 16 | 1120 | 80 | 90 | 100 | 90 | 85 | 85 | 100 | 90 |
| 32 | 1120 | 95 | 90 | 99 | 90 | 95 | 95 | 100 | 90 |
| 8 | 2240 | 60 | 55 | 95 | 70 | 80 | 65 | 100 | 79 |
| 16 | 2240 | 95 | 90 | 95 | 90 | 90 | 85 | 100 | 93 |
| 32 | 2240 | 95 | 90 | 90 | 90 | 99 | 95 | 100 | 93 |

TABLE 12

Synergistic Activity of Foliar-Applied Compound A Benzyl Ester and Cyanazine Herbicidal Compositions on Control of Weeds Common to Rice Cropping Systems.

| Compound A Benzyl Ester | Cyanazine | Visual Weed Control (%) - 20 DAA IPOHE | |
|---|---|---|---|
| g ae/ha | g ai/ha | Obs | Exp |
| 8 | 0 | 20 | — |
| 16 | 0 | 40 | — |
| 32 | 0 | 55 | — |
| 0 | 275 | 50 | — |
| 8 | 275 | 80 | 60 |
| 16 | 275 | 90 | 70 |
| 32 | 275 | 80 | 78 |

TABLE 13

Synergistic Activity of Foliar-Applied Compound A Benzyl Ester and Ioxynil Herbicidal Compositions on Control of Weeds Common to Rice Cropping Systems.

| Compound A Benzyl Ester | Ioxynil | Visual Weed Control (%) - 20 DAA IPOHE | |
|---|---|---|---|
| g ae/ha | g ai/ha | Obs | Exp |
| 8 | 0 | 0 | — |
| 16 | 0 | 15 | — |
| 32 | 0 | 55 | — |
| 0 | 300 | 50 | — |
| 8 | 300 | 50 | 50 |
| 16 | 300 | 90 | 58 |
| 32 | 300 | 90 | 78 |

TABLE 14

Synergistic Activity of Foliar-Applied Compound A Benzyl Ester and Hexazinone Herbicidal Compositions on Control of Weeds Common to Rice Cropping Systems.

| Compound A Benzyl Ester | Hexazinone | Visual Weed Control (%) - 21 DAA ECHCO | |
|---|---|---|---|
| g ae/ha | g ai/ha | Obs | Exp |
| 8 | 0 | 50 | — |
| 16 | 0 | 65 | — |
| 32 | 0 | 85 | — |
| 0 | 625 | 25 | — |
| 0 | 1250 | 55 | — |
| 8 | 625 | 100 | 63 |
| 16 | 625 | 100 | 74 |
| 32 | 625 | 100 | 89 |
| 8 | 1250 | 90 | 78 |
| 16 | 1250 | 100 | 84 |
| 32 | 1250 | 100 | 93 |

| Compound A Benzyl Ester | Hexazinone | Visual Weed Control (%) - 21 DAA | | | |
|---|---|---|---|---|---|
| | | ECHCG | | IPOHE | |
| g ae/ha | g ai/ha | Obs | Exp | Obs | Exp |
| 8 | 0 | 45 | — | 10 | — |
| 16 | 0 | 85 | — | 25 | — |
| 32 | 0 | 90 | — | 60 | — |
| 0 | 625 | 20 | — | 80 | — |
| 8 | 625 | 85 | 56 | 90 | 82 |
| 16 | 625 | 90 | 88 | 99 | 85 |
| 32 | 625 | 90 | 92 | 100 | 92 |

BRAPP     *Brachiaria platyphylla* (Griseb.) Nash     signalgrass, broadleaf
COMBE     *Commelina benghalensis* L.     dayflower, Benghal
CYPIR     *Cyperus iria* L.     flatsedge, rice
CYPES     *Cyperus esculentus* L.     nutsedge, yellow
ECHCG     *Echinochloa crusgalli* (L.) Beauv.     barnyardgrass
ECHCO     *Echinochloa colona* (L.) Link     junglerice
IPOHE     *Ipomoea hederacea* Jacq.     morningglory, ivyleaf
LEFCH     *Leptochloa chinensis* (L.) Nees     sprangletop, Chinese
g ae/ha = grams acid equivalent per hectare
g ai/ha = grams active ingredient per hectare
Obs = observed value
Exp = expected value as calculated by Colby's equation
DAA = days after application Example II Evaluation of in-Water Applied Herbicidal Mixtures for Weed Control in Transplanted Paddy Rice Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters ($cm^2$) leaving a headspace of 3 centimeters (cm) in each pot Mud was allowed to dry overnight prior to planting or transplanting. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 840 mL of mud contained in 32-oz. non-perforated plastic pots with a surface area of 86.59 $cm^2$ 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 h photoperiod which was maintained at about 29° C during the day and 26° C. during the night. Nutrients were added as Osmocote® (19:6:12, N:P:K+ minor nutrients) at 2 g per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl)pyridine-2-carboxylic acid (compound A) each formulated as an SC (suspension concentrate) and various herbicidal components alone and in combination. Forms of compound A were applied on an acid equivalent basis.

Forms of compound A (compound of formula I) tested include:

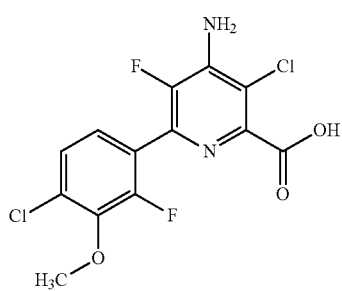

Compound A Acid

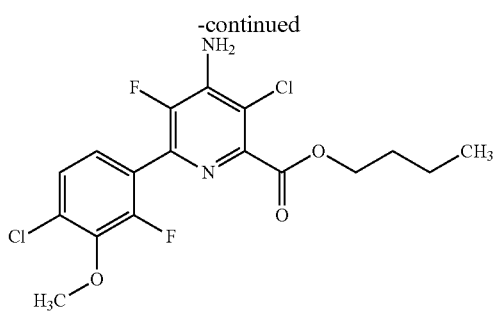

Compound A n-Butyl Ester

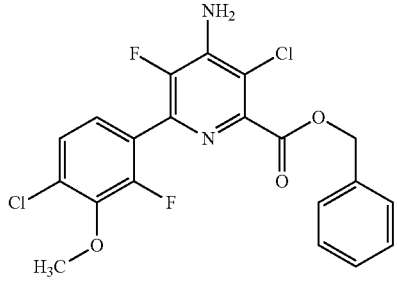

Compound A Benzyl Ester

Other herbicidal components were applied on an active ingredient basis and included photosystem II (PSII)-inhibits propanil formulated as Stain® 4M EC bentazon-sodium formulated as Basagran®, and simetryne (technical grade material).

Treatment requirements for each compound or herbicidal component were calculated based upon the rates being tested, the concentration of active ingredient or acid equivalent in the formulation, an application volume of 2 mL per component per pot, and an application area of 86.59 cm² per pot.

For formulated compounds, a measured amount was placed in an individual 100 or 200 mL glass vial and was dissolved in a volume of 1.25% (v/v) Agri-Dex® crop oil concentrate to obtain application solutions. If the test compound did not dissolve readily, the mixture was warmed and/or sonicated.

For technical grade compounds, a weighed amount was placed in an individual 100 to 200 mL glass vial and was dissolved in a volume of acetone to obtain concentrated stock solutions. If the test compound did not dissolve readily, the mixture was warmed and/or sonicated. The concentrated stock solutions obtained were diluted with an equivalent volume of an aqueous mixture containing 2.5% (v/v) crop oil concentrate so that the final application solutions contained 1.25% (v/v) crop oil concentrate.

Applications were made by injecting with a pipetter appropriate amounts of the application solutions, individually and sequentially, into the aqueous layer of the paddy. Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 15-20.

TABLE 15

Synergistic Activity of In-Water Applications of Compound A Acid and Propanil Herbicidal Compositions on Weed Control in a Rice Cropping System.

| Compound A Acid | Propanil | Visual Weed Control (%) - 21 DAA SCPMA | |
|---|---|---|---|
| g ae/ha | g ai/ha | Obs | Exp |
| 8.75 | 0 | 0 | — |
| 17.5 | 0 | 0 | — |
| 35 | 0 | 0 | — |
| 0 | 1680 | 50 | — |
| 0 | 3360 | 90 | — |
| 8.75 | 1680 | 50 | 50 |
| 17.5 | 1680 | 100 | 50 |
| 35 | 1680 | 100 | 50 |
| 8.75 | 3360 | 100 | 90 |
| 17.5 | 3360 | 100 | 90 |
| 35 | 3360 | 100 | 90 |

TABLE 16

Synergistic Activity of In-Water Applications of Compound A Benzyl Ester and Propanil Herbicidal Compositions on Weed Control in a Rice Cropping System.

| Compound A Benzyl Ester | Propanil | Visual Weed Control (%) - 21 DAA SCPMA | |
|---|---|---|---|
| g ae/ha | g ai/ha | Obs | Exp |
| 8.75 | 0 | 0 | — |
| 17.5 | 0 | 0 | — |
| 35 | 0 | 0 | — |
| 0 | 1680 | 50 | — |
| 0 | 3360 | 90 | — |
| 8.75 | 1680 | 99 | 50 |
| 17.5 | 1680 | 100 | 50 |
| 35 | 1680 | 70 | 50 |
| 8.75 | 3360 | 100 | 90 |
| 17.5 | 3360 | 100 | 90 |
| 35 | 3360 | 100 | 90 |

TABLE 17

Synergistic Activity of In-Water Applications of Compound A Acid and Bentazon-sodium Herbicidal Compositions on Weed Control in a Rice Cropping System.

| Compound A Acid | Bentazon-sodium | Visual Weed Control (%) - 21 DAA | | | |
|---|---|---|---|---|---|
| | | ECHCG | | LEFCH | |
| g ae/ha | g ae/ha | Obs | Exp | Obs | Exp |
| 8.75 | 0 | 0 | — | 0 | — |
| 17.5 | 0 | 0 | — | 0 | — |
| 0 | 420 | 0 | — | 0 | — |
| 0 | 840 | 0 | — | 0 | — |
| 8.75 | 420 | 30 | 0 | 20 | 0 |
| 17.5 | 420 | 20 | 0 | 30 | 0 |
| 8.75 | 840 | 10 | 0 | 30 | 0 |
| 17.5 | 840 | 25 | 0 | 40 | 0 |

| Compound A Acid | Bentazon-sodium | Visual Weed Control (%) - 20 DAA | | | |
|---|---|---|---|---|---|
| | | LEFCH | | SCPMA | |
| g ae/ha | g ae/ha | Obs | Exp | Obs | Exp |
| 42.4 | 0 | 15 | — | 0 | — |
| 84.8 | 0 | 55 | — | 0 | — |
| 0 | 1120 | 0 | — | 0 | — |
| 42.4 | 1120 | 38 | 15 | 80 | 0 |
| 84.8 | 1120 | 63 | 55 | 100 | 0 |

TABLE 18

Synergistic Activity of In-Water Applications of Compound A Benzyl Ester and Bentazon-sodium Herbicidal Compositions on Weed Control in a Rice Cropping System.

| Compound A Benzyl Ester | Bentazon-sodium | | |
|---|---|---|---|
| g ae/ha | g ae/ha | Obs | Exp |
| | | Visual Weed Control (%) - 21 DAA LEFCH | |
| 8.75 | 0 | 20 | — |
| 17.5 | 0 | 30 | — |
| 35 | 0 | 55 | — |
| 0 | 420 | 0 | — |
| 0 | 840 | 0 | — |
| 8.75 | 420 | 30 | 20 |
| 17.5 | 420 | 50 | 30 |
| 35 | 420 | 70 | 55 |
| 8.75 | 840 | 50 | 20 |
| 17.5 | 840 | 65 | 30 |
| 35 | 840 | 50 | 55 |
| | | Visual Weed Control (%) - 20 DAA LEFCH | |
| 70 | 0 | 80 | — |
| 0 | 1120 | 0 | — |
| 70 | 1120 | 93 | 80 |
| | | Visual Weed Control (%) - 20 DAA SCPMA | |
| 35 | 0 | 0 | — |
| 70 | 0 | 0 | — |
| 0 | 1120 | 0 | — |
| 35 | 1120 | 100 | 0 |
| 70 | 1120 | 43 | 0 |

TABLE 19

Synergistic Activity of In-Water Applications of Compound A n-Butyl Ester and Bentazon-sodium Herbicidal Compositions on Weed Control in a Rice Cropping System.

| Compound A n-Butyl Ester | Bentazon-sodium | Visual Weed Control (%) - 20 DAA | |
|---|---|---|---|
| g ae/ha | g ae/ha | Obs | Exp |
| | | ECHOR | |
| 70 | 0 | 40 | — |
| 0 | 1120 | 0 | — |
| 70 | 1120 | 60 | 40 |
| | | SCPMA | |
| 35 | 0 | 0 | — |
| 70 | 0 | 0 | — |
| 0 | 1120 | 0 | — |
| 35 | 1120 | 100 | 0 |
| 70 | 1120 | 50 | 0 |

TABLE 20

Synergistic Activity of In-Water Applications of Compound A Benzyl Ester and Simetryne Herbicidal Compositions on Weed Control in a Rice Cropping System.

| Compound A Benzyl Ester | Simetryne | Visual Weed Control (%) - 19 DAA | | | |
|---|---|---|---|---|---|
| | | ECHOR | | FIMMI | |
| g ae/ha | g ai/ha | Obs | Exp | Obs | Exp |
| 8 | 0 | 10 | — | 0 | — |
| 16 | 0 | 20 | — | 0 | — |
| 32 | 0 | 25 | — | 85 | — |
| 0 | 112.5 | 0 | — | 45 | — |
| 0 | 225 | 10 | — | 90 | — |
| 8 | 112.5 | 20 | 10 | 100 | 45 |
| 16 | 112.5 | 50 | 20 | 100 | 45 |
| 32 | 112.5 | 20 | 25 | 100 | 92 |
| 8 | 225 | 50 | 19 | 100 | 90 |
| 16 | 225 | 50 | 28 | 100 | 90 |
| 32 | 225 | 100 | 33 | 100 | 99 |

| Compound A Benzyl Ester | Simetryne | Visual Weed Control (%) - 19 DAA | |
|---|---|---|---|
| | | CYPRO | |
| g ae/ha | g ai/ha | Obs | Exp |
| 8 | 0 | 50 | — |
| 16 | 0 | 85 | — |
| 32 | 0 | 90 | — |
| 0 | 112.5 | 0 | — |
| 0 | 225 | 0 | — |
| 0 | 450 | 0 | — |
| 8 | 112.5 | 90 | 50 |
| 16 | 112.5 | 100 | 85 |
| 32 | 112.5 | 100 | 90 |
| 8 | 225 | 80 | 50 |
| 16 | 225 | 85 | 85 |
| 32 | 225 | 100 | 90 |
| 8 | 450 | 85 | 50 |
| 16 | 450 | 100 | 85 |
| 32 | 450 | 100 | 90 |

| | | | |
|---|---|---|---|
| CYPRO | *Cyperus rotundus* L. | | nutsedge, purple |
| ECHCG | *Echinochloa crusgalli* (L.) Beauv. | | barnyardgrass |
| ECHOR | *Echinochloa oryzoides* (Ard.) Fritsch | | watergrass, early |
| FIMMI | *Fimbristylis miliacea* (L.) Vahl | | fringerush, globe |

-continued

| LEFCH | *Leptochloa chinensis* (L.) Nees | sprangletop, Chinese |
| SCPMA | *Schoenoplectus maritimus* (L.) Lye | clubrush, sea | g ae/ha = grams acid equivalent per hectare
g ai/ha = grams active ingredient per hectare
Obs = observed value
Exp = expected value as calculated by Colby's equation
DAA = days after application Example III Evaluation of Postemergence Herbicidal Activity of Mixtures in Cereal Crops in the Greenhouse Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days in a greenhouse with an approximate 14 hour photoperiod which was maintained at about 18° C. during the day and about 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of the benzyl ester of 4-amino-3-chloro-5-fluoro-6-(4-chloro-2-fluoro-3-methoxy-phenyl)pyridine-2-carboxylic acid (Compound A), formulated as an SC, a second cereal herbicide alone and then both in combination.

Forms of Compound A (Compound of Formula I) Tested Include:

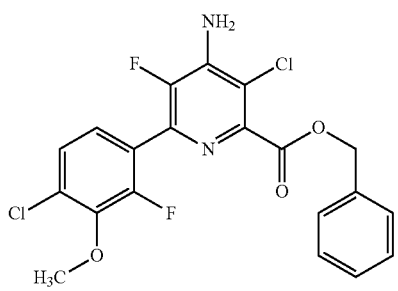

Compound A Benzyl Ester

Other herbicidal components were applied on an active ingredient basis and included PSII-inhibiting herbicides.

Measured aliquots of benzyl ester of 4-amino-3-chloro-5-fluoro-6-(4-chloro-2-fluoro-3-methoxy-phenyl)pyridine-2-carboxylic acid (Compound A) were placed in 25 milliliter (mL) glass vials and diluted in a volume of 1.25% (v/v) Agri-Dex® crop oil concentrate to obtain stock solutions. Compound requirements are based upon a 12 mL application volume at a rate of 187 liters per hectare (L/ha). Spray solutions of the second cereal herbicide and experimental compound mixtures were prepared by adding the stock solutions to the appropriate amount of dilution solution to form 12 mL spray solution with active ingredients in two- and three-way combinations. Formulated compounds were applied to the plant material with an overhead Mandel track sprayer equipped with an 8002E nozzle calibrated to deliver 187 L/ha over an application area of 0.503 square meters ($m^2$) at a spray height of 18 inches (46 cm) above average plant canopy. Control plants were sprayed in the same manner with the solvent blank.

The treated plants and control plants were placed in a greenhouse as described above and watered by sub-irrigation to prevent wash-off of the test compounds. After 20-22 days, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 21-22.

TABLE 21

Synergistic Activity of Foliar-Applied Compound A Benzyl Ester and Metribuzin Herbicidal Compositions on Weed Control in a Cereals Cropping System.

| Compound A | | Visual Weed Control (%)-21 DAA | | | | | |
| Benzyl Ester | Metribuzin | SASKR | | KCHSC | | LAMPU | |
| g ai/ha | g ai/ha | Obs | Exp | Obs | Exp | Obs | Exp |
| 2.5 | 0 | 15 | — | 20 | — | 80 | — |
| 5 | 0 | 50 | — | 41 | — | 86 | — |
| 10 | 0 | 67 | — | 62 | — | 94 | — |
| 0 | 25 | 8 | — | 0 | — | 3 | — |

TABLE 21-continued

Synergistic Activity of Foliar-Applied Compound
A Benzyl Ester and Metribuzin Herbicidal Compositions
on Weed Control in a Cereals Cropping System.

| 0    | 50  | 8   | —  | 8   | —  | 15  | —  |
|------|-----|-----|----|-----|----|-----|----|
| 0    | 100 | 67  | —  | 88  | —  | 23  | —  |
| 2.5  | 25  | 25  | 21 | 45  | 20 | 90  | 81 |
| 2.5  | 50  | 20  | 21 | 35  | 26 | 89  | 83 |
| 5    | 25  | 38  | 54 | 58  | 41 | 91  | 86 |
| 5    | 50  | 63  | 54 | 43  | 45 | 98  | 88 |
| 5    | 100 | 100 | 83 | 100 | 93 | 99  | 89 |
| 10   | 100 | 97  | 89 | 100 | 96 | 100 | 95 |

| Compound A | | Visual Weed Control (%)-21 DAA | | | |
|---|---|---|---|---|---|
| Benzyl Ester | Metribuzin | CHEAL | | SINAR | |
| g ai/ha | g ai/ha | Obs | Exp | Obs | Exp |
| 2.5 | 0  | 50 | —  | 70 | —  |
| 5   | 0  | 58 | —  | 73 | —  |
| 0   | 25 | 0  | —  | 8  | —  |
| 0   | 50 | 55 | —  | 15 | —  |
| 2.5 | 25 | 68 | 50 | 90 | 72 |
| 2.5 | 50 | 70 | 78 | 95 | 75 |
| 5   | 25 | 78 | 58 | 93 | 75 |
| 5   | 50 | 83 | 81 | 95 | 77 |

TABLE 22

Synergistic Activity of Foliar-Applied Compound A Benzyl Ester
and Isoproturon Herbicidal Compositions on Weed Control in a
Cereals Cropping System.

| Compound A Benzyl Ester | Isoproturon | Visual Weed Control (%) - 21 DAA | | | |
|---|---|---|---|---|---|
| g ai/ha | g ai/ha | Obs | Exp | Obs | Exp |
| | | AMARE | | SINAR | |
| 2.5 | 0    | 20 | —  | 70 | —  |
| 5   | 0    | 38 | —  | 73 | —  |
| 0   | 375  | 3  | —  | 13 | —  |
| 0   | 750  | 10 | —  | 40 | —  |
| 2.5 | 375  | 43 | 22 | 84 | 74 |
| 2.5 | 750  | 60 | 28 | 88 | 82 |
| 5   | 375  | 55 | 39 | 89 | 76 |
| 5   | 750  | 70 | 44 | 84 | 84 |
| | | GALAP | | VERPE | |
| 5   | 0    | 66 | —  | 17 | —  |
| 10  | 0    | 77 | —  | 23 | —  |
| 0   | 375  | 5  | —  | 8  | —  |
| 0   | 750  | 5  | —  | 10 | —  |
| 0   | 1500 | 27 | —  | 13 | —  |
| 5   | 375  | 68 | 68 | 18 | 23 |
| 5   | 750  | 80 | 68 | 28 | 25 |
| 5   | 1500 | 99 | 75 | 60 | 28 |
| 10  | 1500 | 97 | 83 | 70 | 34 |

| Compound A Benzyl Ester | Isoproturon | Visual Weed Control (%) - 21 DAA LAMPU | |
|---|---|---|---|
| g ai/ha | g ai/ha | Obs | Exp |
| 2.5 | 0    | 80 | —  |
| 5   | 0    | 86 | —  |
| 10  | 0    | 94 | —  |
| 0   | 375  | 3  | —  |
| 0   | 750  | 3  | —  |
| 0   | 1500 | 13 | —  |
| 2.5 | 375  | 83 | 81 |
| 2.5 | 750  | 89 | 81 |
| 5   | 375  | 89 | 86 |
| 5   | 750  | 91 | 86 |
| 5   | 1500 | 97 | 88 |
| 10  | 1500 | 97 | 95 |

| AMARE | *Amaranthus retroflexus* L. | pigweed, redroot |
| CHEAL | *Chenopodium album* L. | lambsquarters, common |
| GALAP | *Galium aparine* L. | bedstraw, catchweed |
| KCHSC | *Kochia scoparia* (L.) Schrad. | kochia |
| LAMPU | *Lamium purpureum* L. | deadnettle, purple |
| SASKR | *Salsola tragus* L. | thistle, Russian |
| SINAR | *Sinapis arvensis* L. | mustard, wild |
| VERPE | *Veronica persica* Poir. | Speedwell, Persian | g ae/ha = grams acid equivalent per hectare
g ai/ha = grams active ingredient per hectare
Obs = observed value
Exp = expected value as calculated by Colby's equation
DAA = days after application Example IV Evaluation of Pre-emergence Soil-Applied
Herbicidal Mixtures for Weed Control Seeds or nutlets of the desired test plant species were planted in a soil matrix prepared by mixing a loam soil (32 percent silt, 23 percent clay, and 45 percent sand, with a pH of about 6.5 and an organic matter content of about 1.9 percent) and calcareous grit in an 80 to 20 ratio. The soil matrix was contained in plastic pots with a volume of 1 quart and a surface area of 83.6 square centimeters ($cm^2$).

Treatments consisted of the benzyl ester of 4-amino-3-chloro-5-fluoro-6-(4-chloro-2-fluoro-3-methoxy-phenyl)pyridine-2-carboxylic acid (compound A) formulated as an SC (suspension concentrate) and various herbicidal components alone and in combination. Forms of compound A were applied on an acid equivalent basis.

Forms of compound A (compound of formula I) tested include:

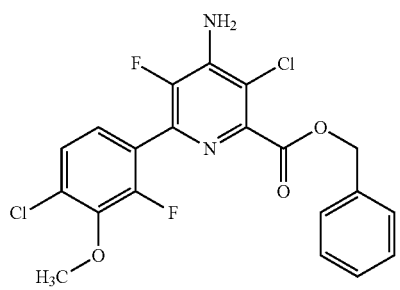

Compound A Benzyl Ester

Other herbicidal components were applied on an acid equivalent or active ingredient basis and included the PSII-inhibiting herbicides, atrazine formulated as Atrazine® 90WDG, metribuzin formulated as Metribuzin 75DF, simazine formulated as Princep Caliber 90, tebuthiuron formulated as Spike 80DF, cyanazine (technical grade material), hexazinone (technical grade material), linuron (technical grade material), terbuthylazine (technical grade material), and diuron formulated as Diuron 4L.

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrate (COC) to obtain 12x stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) COC so that the final spray solutions contained 1.25% (v/v) COC.

For treatments comprised of technical compounds, weighed amounts can be placed individually in 25 mL glass vials and dissolved in a volume of 97:3 (v/v) acetone/DMSO to obtain 12x stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) COC so that the final spray solutions contain 1.25% (v/v) COC. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials can be placed individually in 25 mL glass vials and dissolved in a volume of 97:3 (v/v) acetone/DMSO to obtain 12x stock solutions, and measured amounts of the formulated compounds can be placed individually in 25 mL glass vials and diluted in a volume of 1.5% (v/v) COC or water to obtain 12x stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of an appropriate amount of an aqueous mixture of 1.5% (v/v) COC so that the final spray solutions contain 1.25% (v/v) COC. As required, additional water and/or 97:3 (v/v) acetone/DMSO can be added to individual application solutions so that the final acetone and DMSO concentrations of the application solutions being compared are 8.1% and 0.25%, respectively.

All stock solutions and applications solutions were visually inspected for compound compatibility prior to application. Spray solutions were applied to the soil with an overhead Mandel track sprayer equipped with a 8002E nozzles calibrated to deliver 187 L/ha over an application area of 0.503 $m^2$ at a spray height of 18 inches (46 cm) above average pot height. Control pots were sprayed in the same manner with the solvent blank.

The treated and control pots were placed in a greenhouse and top watered as needed. When required to ensure good germination and healthy plants, a fungicide treatment and/or other chemical or physical treatment was applied. The pots were maintained in a greenhouse with an approximate 14 hr photoperiod which was maintained at about 29° C. during the day and 26° C. during the night. Nutrients (Peters® Excel 15-5-15 5-Ca 2-Mg) were applied in the irrigation solution as needed and water was added on a regular basis. Supplemental lighting was provided with overhead metal halide 1000-Watt lamps as necessary. After approximately 4 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 23-30.

TABLE 23

Synergistic Activity of Soil-applied, Pre-emergence Applications of Compound A Benzyl Ester and Atrazine Herbicidal Compositions on Weed Control

| Compound A Benzyl Ester | Atrazine | Visual Weed Control (%) - 32 DAA XANST | |
|---|---|---|---|
| g ae/ha | g ai/ha | Obs | Exp |
| 8 | 0 | 33 | — |
| 16 | 0 | 35 | — |
| 32 | 0 | 65 | — |
| 0 | 560 | 68 | — |
| 0 | 1120 | 40 | — |
| 8 | 560 | 95 | 78 |
| 16 | 560 | 100 | 79 |
| 32 | 560 | 75 | 89 |
| 8 | 1120 | 100 | 60 |

TABLE 23-continued

Synergistic Activity of Soil-applied, Pre-emergence Applications of Compound A Benzyl Ester and Atrazine Herbicidal Compositions on Weed Control

| Compound A Benzyl Ester | Atrazine | Visual Weed Control (%) - 32 DAA XANST | |
|---|---|---|---|
| g ae/ha | g ai/ha | Obs | Exp |
| 16 | 1120 | 100 | 61 |
| 32 | 1120 | 100 | 79 |

TABLE 24

Synergistic Activity of Soil-applied, Pre-emergence Applications of Compound A Benzyl Ester and Metribuzin Herbicidal Compositions on Weed Control

| Compound A Benzyl Ester | Metribuzin | Visual Weed Control (%) - 27 DAA SETFA | |
|---|---|---|---|
| g ae/ha | g ai/ha | Obs | Exp |
| 16 | 0 | 8 | — |
| 32 | 0 | 15 | — |
| 0 | 210 | 43 | — |
| 0 | 420 | 83 | — |
| 16 | 210 | 100 | 48 |
| 32 | 210 | 100 | 52 |
| 16 | 420 | 95 | 85 |
| 32 | 420 | 100 | 86 |

TABLE 25

Synergistic Activity of Soil-applied, Pre-emergence Applications of Compound A Benzyl Ester and Simazine Herbicidal Compositions on Weed Control

| Compound A Benzyl Ester | Simazine | Visual Weed Control (%) - 33 DAA XANST | |
|---|---|---|---|
| g ae/ha | g ai/ha | Obs | Exp |
| 16 | 0 | 38 | — |
| 32 | 0 | 35 | — |
| 0 | 1120 | 70 | — |
| 0 | 2240 | 92 | — |
| 16 | 1120 | 77 | 82 |
| 32 | 1120 | 95 | 81 |
| 16 | 2240 | 100 | 95 |
| 32 | 2240 | 100 | 95 |

TABLE 26

Synergistic Activity of Soil-applied, Pre-emergence Applications of Compound A Benzyl Ester and Tebuthiuron Herbicidal Compositions on Weed Control

| Compound A Benzyl Ester | Tebuthiuron | Visual Weed Control (%) - 33 DAA IPOHE | |
|---|---|---|---|
| g ae/ha | g ai/ha | Obs | Exp |
| 16 | 0 | 0 | — |
| 32 | 0 | 5 | — |
| 0 | 420 | 87 | — |

TABLE 26-continued

Synergistic Activity of Soil-applied, Pre-emergence Applications of Compound A Benzyl Ester and Tebuthiuron Herbicidal Compositions on Weed Control

| Compound A Benzyl Ester | Tebuthiuron | Obs | Exp |
|---|---|---|---|
| g ae/ha | g ai/ha | | |
| 0 | 840 | 90 | — |
| 16 | 420 | 93 | 87 |
| 32 | 420 | 93 | 87 |
| 16 | 840 | 100 | 90 |
| 32 | 840 | 100 | 91 |

| | | Visual Weed Control (%) - 29 DAA XANST | |
|---|---|---|---|
| 16 | 0 | 0 | — |
| 32 | 0 | 5 | — |
| 0 | 210 | 40 | — |
| 0 | 3360 | 95 | — |
| 16 | 210 | 63 | 40 |
| 32 | 210 | 55 | 43 |
| 16 | 3360 | 100 | 95 |
| 32 | 3360 | 100 | 95 |

TABLE 27

Synergistic Activity of Soil-applied, Pre-emergence Applications of Compound A Benzyl Ester and Cyanazine Herbicidal Compositions on Weed Control

| Compound A Benzyl Ester | Cyanazine | Visual Weed Control (%) - 27 DAA BRAPP | |
|---|---|---|---|
| g ae/ha | g ai/ha | Obs | Exp |
| 32 | 0 | 0 | — |
| 0 | 170 | 0 | — |
| 0 | 440 | 15 | — |
| 0 | 880 | 10 | — |
| 16 | 220 | 0 | 0 |
| 32 | 220 | 10 | 0 |
| 32 | 440 | 28 | 15 |
| 32 | 880 | 40 | 10 |

TABLE 28

Synergistic Activity of Soil-applied, Pre-emergence Applications of Compound A Benzyl Ester and Linuron Herbicidal Compositions on Weed Control

| Compound A Benzyl Ester | Linuron | Visual Weed Control (%) - 27 DAA BRAPP | |
|---|---|---|---|
| g ae/ha | g ai/ha | Obs | Exp |
| 16 | 0 | 0 | — |
| 32 | 0 | 0 | — |
| 0 | 620 | 0 | — |
| 16 | 620 | 15 | 0 |
| 32 | 620 | 20 | 0 |

TABLE 29

Synergistic Activity of Soil-applied, Pre-emergence Applications of Compound A Benzyl Ester and Tebuthylazine Herbicidal Compositions on Weed Control

| Compound A Benzyl Ester | Terbuthylazine | Visual Weed Control (%) - 27 DAA XANST | |
|---|---|---|---|
| g ae/ha | g ai/ha | Obs | Exp |
| 16 | 0 | 10 | — |
| 32 | 0 | 25 | — |
| 0 | 1000 | 45 | — |
| 16 | 1000 | 83 | 51 |
| 32 | 1000 | 75 | 59 |

TABLE 30

Synergistic Activity of Soil-applied, Pre-emergence Applications of Compound A Benzyl Ester and Diuron Herbicidal Compositions on Weed Control

| Compound A Benzyl Ester | Diuron | Visual Weed Control (%)-29 DAA ABUTH | |
|---|---|---|---|
| g ae/ha | g ai/ha | Obs | Exp |
| 16 | 0 | 65 | — |
| 32 | 0 | 93 | — |
| 0 | 280 | 30 | — |
| 0 | 560 | 70 | — |
| 0 | 1120 | 90 | — |
| 16 | 280 | 90 | 76 |
| 32 | 280 | 100 | 95 |
| 16 | 560 | 100 | 90 |
| 32 | 560 | 100 | 98 |
| 16 | 1120 | 100 | 97 |
| 32 | 1120 | 100 | 99 |

| Compound A Benzyl Ester | Diuron | Visual Weed Control (%)-28 DAA | | | |
|---|---|---|---|---|---|
| | | BRAPP | | ECHCG | |
| g ae/ha | g ai/ha | Obs | Exp | Obs | Exp |
| 16 | 0 | 0 | — | 0 | — |
| 32 | 0 | 5 | — | 0 | — |
| 0 | 280 | 0 | — | 25 | — |
| 0 | 560 | 35 | — | 65 | — |
| 16 | 280 | 45 | 0 | 35 | 25 |
| 32 | 280 | 25 | 5 | 23 | 25 |
| 16 | 560 | 100 | 35 | 80 | 65 |
| 32 | 560 | 100 | 38 | 98 | 65 |

| Compound A Benzyl Ester | Diuron | Visual Weed Control (%)-29 DAA | | | | | |
|---|---|---|---|---|---|---|---|
| | | ECHCO | | SETFA | | SETVI | |
| g ae/ha | g ai/ha | Obs | Exp | Obs | Exp | Obs | Exp |
| 16 | 0 | 0 | — | 0 | — | 10 | — |
| 32 | 0 | 5 | — | 0 | — | 10 | — |
| 0 | 280 | 15 | — | 5 | — | 0 | — |
| 16 | 280 | 60 | 15 | 13 | 5 | 48 | 10 |
| 32 | 280 | 80 | 19 | 30 | 5 | 25 | 10 |

| | | |
|---|---|---|
| ABUTH | *Abutilon theophrasti* Medik. | velvetleaf |
| BRAPP | *Brachiaria platyphylla* (Groseb.) Nash or *Urochloa platyphylla* (Nash) R. D. Webster | signalgrass, broadleaf |
| ECHCG | *Echinochloa crus-galli* (L.) P. Beauv. | barnyardgrass |
| ECHCO | *Echinochloa colonum* (L.) Link | junglerice |
| IPOHE | *Ipomoea hederacea* (L.) Jacq. | morningglory, ivyleaf |
| SETFA | *Setaria faberi* Herrm. | foxtail, giant |
| SETVI | *Setaria viridis* (L.) Beauv. | foxtail, green |
| XANST | *Xanthium strumarium* L. | cocklebur, common | g ae/ha = grams acid equivalent per hectare
g ai/ha = grams active ingredient per hectare TABLE 30-continued Synergistic Activity of Soil-applied,
Pre-emergence Applications of Compound A Benzyl
Ester and Diuron Herbicidal Compositions on Weed Control Obs = observed value
Exp = expected value as calculated by Colby's equation
DAA = days after application

What is claimed is:

1. A synergistic herbicidal composition comprising a herbicidally effective amount of (a) a compound of the formula (I):

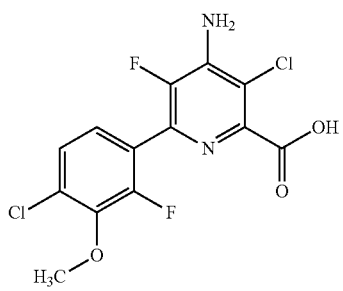

or an alkyl or benzyl ester, or an agriculturally acceptable salt of formula (I) and (b) atrazine, bentazon, bromoxynil, chlorotoluron, cyanazine, diuron, hexazinone, ioxynil, isoproturon, linuron, metribuzin, propanil, siduron, simazine, simetryne, tebuthiuron or terbuthylazine or agriculturally acceptable salt or ester thereof, wherein (a) and (b) are present in the composition in a ratio such that the composition exhibits herbicidal synergy.

2. The composition of claim 1, wherein (a) is a $C_{1-4}$ alkyl or benzyl ester of the compound of formula (I).

3. The composition of claim 1, wherein (a) is a $C_{1-4}$ alkyl ester of the compound of formula (I).

4. The composition of claim 2, wherein (a) is a benzyl ester of the compound of formula (I).

5. The composition of claim 1, wherein (a) is the carboxylic acid of the compound of formula (I).

6. The composition of claim 1, further comprising at least one compound selected from the group consisting of agriculturally acceptable, herbicide safeners, adjuvants, and carriers.

7. A method of controlling undesirable vegetation, comprising the steps of:
contacting a plant, wherein the plant is undesirable vegetation, or the locus thereof, soil or water, wherein the soil or the water allows for the growth of the undesirable vegetation, with a herbicidally effective amount of a combination comprising (a) a compound of the formula (I):

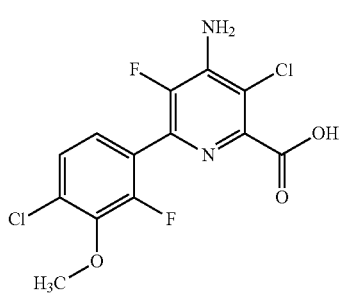

or an alkyl or benzyl ester, or an agriculturally acceptable salt of formula (I) and (b) atrazine, bentazon, bromoxynil, chlorotoluron, cyanazine, diuron, hexazinone, ioxynil, isoproturon, linuron, metribuzin, propanil, siduron, simazine, simetryne, tebuthiuron or terbuthylazine or agriculturally acceptable salt or ester thereof, wherein (a) and (b) are present in the combination in a ratio such that the combination exhibits herbicidal synergy; wherein the undesirable vegetation is controlled in direct-seeded, water-seeded and transplanted rice, cereals, wheat, barley, oats, rye, sorghum, maize and canola.

8. The method of claim 7, wherein the (a) and (b) are applied to water.

9. The method of claim 8, wherein the water is part of a flooded rice paddy.

10. The method of claim 7, wherein the (a) and (b) are applied pre-emergently to the undesirable vegetation in a crop.

11. The method of claim 7, wherein the (a) and (b) are applied post-emergently to the undesirable vegetation in a crop.

12. The method of claim 7, wherein the undesirable vegetation is controlled in glyphosate-, 5-enolpyruvylshikimate-3-phosphate synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase inhibitor-, imidazolinone-, sulfonylurea-, pyrimidinylthiobenzoate-, triazolopyrimidine-, sulfonylaminocarbonyltriazolinone-, acetolactate synthase or acetohydroxy acid synthase inhibitors-, 4-hydroxyphenyl-pyruvate dioxygenase inhibitor-, phytoene desaturase inhibitor-, carotenoid biosynthesis inhibitor-, protoporphyrinogen oxidase inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, triazine-, or bromoxynil- tolerant crops.

13. The method of claim 12, wherein the tolerant crop possesses multiple or stacked traits conferring tolerance to multiple herbicides.

14. The method of claim 7, wherein the undesirable vegetation comprises a herbicide resistant or tolerant plant.

15. The method of claim 14, wherein the resistant or tolerant plant is resistant or tolerant to multiple herbicides.

16. The method of claim 14, wherein the resistant or tolerant plant is resistant or tolerant to acetolactate synthase or acetohydroxy acid synthase inhibitors, photosystem II inhibitors, acetyl CoA carboxylase inhibitors, synthetic auxins, auxin transport inhibitors, photosystem I inhibitors, 5-enolpyruvylshikimate-3-phosphate synthase inhibitors, microtubule assembly inhibitors, fatty acid and lipid synthesis inhibitors, protoporphyrinogen oxidase inhibitors, carotenoid biosynthesis inhibitors, very long chain fatty acid inhibitors, phytoene desaturase inhibitors, glutamine synthetase inhibitors, 4-hydroxyphenyl-pyruvate-dioxygenase inhibitors, mitosis inhibitors, cellulose biosynthesis inhibitors, herbicides with multiple modes-of-action, quinclorac, arylaminopropionic acids, difenzoquat, endothall, or organoarsenicals.

* * * * *